US012622897B2

(12) United States Patent
Boinpally et al.

(10) Patent No.: US 12,622,897 B2
(45) Date of Patent: May 12, 2026

(54) METHODS OF TREATING MIGRAINE

(71) Applicant: Allergan Pharmaceuticals International Limited, Dublin (IE)

(72) Inventors: Ramesh Boinpally, Princeton, NJ (US); Joel Trugman, Hoboken, NJ (US)

(73) Assignee: Allergan Pharmaceuticals International Limited, Dublin (IE)

( * ) Notice: Subject to any disclaimer, the term of this patent is extended or adjusted under 35 U.S.C. 154(b) by 0 days.

(21) Appl. No.: 19/055,916

(22) Filed: Feb. 18, 2025

(65) Prior Publication Data

US 2025/0186413 A1 Jun. 12, 2025

Related U.S. Application Data

(62) Division of application No. 17/953,536, filed on Sep. 27, 2022, now Pat. No. 12,350,259.

(60) Provisional application No. 63/395,134, filed on Aug. 4, 2022, provisional application No. 63/336,843, filed on Apr. 29, 2022, provisional application No. 63/261,782, filed on Sep. 28, 2021, provisional application No. 63/261,783, filed on Sep. 28, 2021, provisional application No. 63/261,731, filed on Sep. 27, 2021.

(51) Int. Cl.

| | |
|---|---|
| ***A61K 31/4375*** | (2006.01) |
| ***A61K 31/496*** | (2006.01) |
| ***A61K 45/06*** | (2006.01) |
| ***A61P 25/06*** | (2006.01) |

(52) U.S. Cl.

CPC ........ *A61K 31/4375* (2013.01); *A61K 31/496* (2013.01); *A61K 45/06* (2013.01); *A61P 25/06* (2018.01)

(58) Field of Classification Search

CPC ............................ A61K 31/4375; A61P 25/06

See application file for complete search history.

(56) References Cited

U.S. PATENT DOCUMENTS

| | | | |
|---|---|---|---|
| 4,166,452 | A | 9/1979 | Generales, Jr. |
| 4,256,108 | A | 3/1981 | Theeuwes |
| 4,265,874 | A | 5/1981 | Bonsen et al. |
| 5,914,129 | A | 6/1999 | Mauskop |
| 7,205,293 | B2 | 4/2007 | Bell et al. |
| 7,390,798 | B2 | 6/2008 | Williams et al. |
| 7,629,338 | B2 | 12/2009 | Wood |
| 7,893,079 | B2 | 2/2011 | Wood et al. |
| 8,481,556 | B2 | 7/2013 | Bell et al. |
| 8,754,096 | B2 | 6/2014 | Bell et al. |
| 8,883,807 | B2 | 11/2014 | Bell et al. |
| 8,895,572 | B2 | 11/2014 | Burgey et al. |
| 8,912,210 | B2 | 12/2014 | Bell et al. |
| 9,067,941 | B2 | 6/2015 | Burgey et al. |
| 9,109,209 | B2 | 8/2015 | Cabirol et al. |
| 9,174,989 | B2 | 11/2015 | Chen et al. |
| 9,227,972 | B2 | 1/2016 | Bell et al. |
| 9,227,973 | B2 | 1/2016 | Bell et al. |
| 9,296,750 | B2 | 3/2016 | Bell et al. |
| 9,376,431 | B2 | 6/2016 | Xiang et al. |
| 9,409,916 | B2 | 8/2016 | Bell et al. |
| 9,487,523 | B2 | 11/2016 | Belyk et al. |
| 9,499,541 | B2 | 11/2016 | Bell et al. |
| 9,499,545 | B2 | 11/2016 | Bell et al. |
| 9,624,478 | B2 | 4/2017 | Cabirol et al. |
| 9,833,448 | B2 | 12/2017 | Bell et al. |
| 9,833,488 | B2 | 12/2017 | Buyuktimkin et al. |
| 9,850,246 | B2 | 12/2017 | Chen et al. |
| 10,106,541 | B2 | 10/2018 | Chen et al. |
| 10,117,836 | B2 | 11/2018 | Johnson et al. |
| 10,117,936 | B2 | 11/2018 | Nebuloni et al. |
| 10,272,077 | B2 | 4/2019 | Bell et al. |
| 11,717,515 | B2 | 8/2023 | Trugman et al. |
| 11,857,542 | B2 | 1/2024 | Trugman et al. |
| 11,925,709 | B2 | 3/2024 | Johnson et al. |
| 12,070,450 | B2 | 8/2024 | Trugman et al. |
| 12,090,148 | B2 | 9/2024 | Trugman et al. |
| 12,168,004 | B2 | 12/2024 | Johnson et al. |
| 12,194,030 | B2 | 1/2025 | Trugman et al. |
| 12,220,408 | B2 | 2/2025 | Johnson et al. |
| 12,310,953 | B2 | 5/2025 | Johnson et al. |
| 12,329,750 | B2 | 6/2025 | Trugman et al. |
| 12,350,259 | B2 | 7/2025 | Boinpally et al. |
| 12,383,545 | B1 | 8/2025 | Trugman et al. |
| 12,458,632 | B2 | 11/2025 | Johnson et al. |
| 12,458,633 | B2 | 11/2025 | Johnson et al. |
| 12,465,598 | B2 | 11/2025 | Boinpally et al. |
| 2004/0076668 | A1 | 4/2004 | Berchielli et al. |

(Continued)

FOREIGN PATENT DOCUMENTS

| | | | |
|---|---|---|---|
| CA | 2479672 | A1 | 10/2003 |
| CN | 101018781 | A | 8/2007 |

(Continued)

OTHER PUBLICATIONS

Ailani et al., "Atogepant for the Preventive Treatment of Migraine", The New England Journal of Medicine, vol. 385, No. 8, pp. 695-706 (2021).*

Sayyah et al., "Statin for Migraine Headache: Is It Worthwhile", Neurology India, vol. 68, No. 5, pp. 1003-1007 (Sep.-Oct. 2020).*

"61st Annual Scientific Meeting", American Headache Society, 208 pages, (Jul. 11-14, 2019).

"Pharmacokinetics in Patients with Impaired Hepatic Function: Study Design, Data Analysis, and Impact on Dosing and Labeling," U.S. Food and Drug Administration (2003).

60th Annual Scientific Meeting, American Headache Society, 60th Annual Scientific Meeting American Headache Society, AHS 2018. San Francisco, CA, United States. Jun. 28-Jul. 1, 2018.

Ailani et al., "An optional second dose of ubrogepant is effective in achieving 2-hour pain freedom in the acute treatment of migraine (166)", Neurology, 94(15), (2020).

(Continued)

*Primary Examiner* — Kevin E Weddington

(74) *Attorney, Agent, or Firm* — Foley Hoag LLP; Hathaway P. Russell; Benjamin A. Vaughan

(57) ABSTRACT

The present disclosure provides methods for the treatment of migraine by the administration of atogepant or a pharmaceutically acceptable salt thereof.

10 Claims, 16 Drawing Sheets

(56) References Cited

U.S. PATENT DOCUMENTS

| | | | |
|---|---|---|---|
| 2005/0196439 | A1 | 9/2005 | Sherwood et al. |
| 2010/0179166 | A1 | 7/2010 | Bell et al. |
| 2010/0227903 | A1 | 9/2010 | Geers et al. |
| 2012/0122899 | A1 | 5/2012 | Bell et al. |
| 2012/0122900 | A1 | 5/2012 | Bell et al. |
| 2012/0122911 | A1 | 5/2012 | Bell et al. |
| 2015/0023888 | A1 | 1/2015 | Cook et al. |
| 2016/0051561 | A1 | 2/2016 | Etter |
| 2016/0220552 | A1 | 8/2016 | Mahjour et al. |
| 2016/0346214 | A1 | 12/2016 | Johnson et al. |
| 2017/0027925 | A1 | 2/2017 | Bell et al. |
| 2017/0189443 | A1 | 7/2017 | Parsons |
| 2018/0008576 | A1 | 1/2018 | Kleideiter et al. |
| 2018/0092899 | A1 | 4/2018 | Liu et al. |
| 2018/0127417 | A1 | 5/2018 | Chen et al. |
| 2019/0070161 | A1 | 3/2019 | Mahjour et al. |
| 2019/0085061 | A1 | 3/2019 | Burstein |
| 2019/0135927 | A1 | 5/2019 | Levin |
| 2019/0209478 | A1 | 7/2019 | Johnson et al. |
| 2019/0374518 | A1 | 12/2019 | Trugman et al. |
| 2019/0374520 | A1 | 12/2019 | Trugman et al. |
| 2020/0383983 | A1 | 12/2020 | Brin et al. |
| 2021/0085612 | A1 | 3/2021 | Johnson et al. |
| 2021/0379029 | A1 | 12/2021 | Trugman et al. |
| 2022/0031686 | A1 | 2/2022 | Trugman et al. |
| 2022/0193051 | A1 | 6/2022 | Trugman et al. |
| 2022/0340650 | A1 | 10/2022 | Jakate et al. |
| 2023/0130736 | A1 | 4/2023 | Boinpally et al. |
| 2023/0158128 | A1 | 5/2023 | Brin et al. |
| 2023/0248655 | A1 | 8/2023 | Johnson et al. |
| 2023/0248715 | A1 | 8/2023 | Liu et al. |
| 2023/0321055 | A1 | 10/2023 | Trugman et al. |
| 2023/0330072 | A1 | 10/2023 | Trugman et al. |
| 2024/0100029 | A1 | 3/2024 | Trugman et al. |
| 2024/0180883 | A1 | 6/2024 | Trugman et al. |
| 2024/0245662 | A1 | 7/2024 | Trugman et al. |
| 2024/0299369 | A1 | 9/2024 | Trugman et al. |
| 2024/0366575 | A1 | 11/2024 | Trugman et al. |
| 2025/0009722 | A1 | 1/2025 | Trugman et al. |
| 2025/0032466 | A1 | 1/2025 | Boinpally et al. |
| 2025/0032467 | A1 | 1/2025 | Boinpally et al. |
| 2025/0064788 | A1 | 2/2025 | Trugman et al. |
| 2025/0177365 | A1 | 6/2025 | Trugman et al. |
| 2025/0186412 | A1 | 6/2025 | Boinpally et al. |
| 2025/0186414 | A1 | 6/2025 | Trugman et al. |
| 2025/0186422 | A1 | 6/2025 | Trugman et al. |
| 2025/0255858 | A1 | 8/2025 | Trugman et al. |
| 2025/0325532 | A1 | 10/2025 | Trugman et al. |
| 2026/0014127 | A1 | 1/2026 | Boinpally et al. |

FOREIGN PATENT DOCUMENTS

| | | | |
|---|---|---|---|
| CN | 101208303 | A | 6/2008 |
| CN | 101448821 | B | 3/2013 |
| JP | 2008/512480 | A | 4/2008 |
| JP | 2008/512481 | A | 4/2008 |
| JP | 2010/529119 | A | 8/2010 |
| JP | 2011/504481 | A | 2/2011 |
| JP | 2012/528827 | A | 11/2012 |
| KR | 10-2013-0087037 | A | 8/2013 |
| RU | 2216317 | C2 | 11/2003 |
| WO | WO-2004/000329 | A1 | 12/2003 |
| WO | WO-2004/082602 | A2 | 9/2004 |
| WO | WO-2004/092166 | A2 | 10/2004 |
| WO | WO-2004/092168 | A1 | 10/2004 |
| WO | WO-2006/031606 | A2 | 3/2006 |
| WO | WO-2006/031610 | A2 | 3/2006 |
| WO | WO-2006/069754 | A1 | 7/2006 |
| WO | WO-2007/092642 | A2 | 8/2007 |
| WO | WO-2007/133491 | A1 | 11/2007 |
| WO | WO-2008/153849 | A1 | 12/2008 |
| WO | WO-2009/050234 | A1 | 4/2009 |
| WO | WO-2009/065922 | A2 | 5/2009 |
| WO | WO-2009/100090 | A1 | 8/2009 |
| WO | WO-2009/126530 | A2 | 10/2009 |
| WO | WO-2010/114801 | A1 | 10/2010 |
| WO | WO-2010/139717 | A1 | 12/2010 |
| WO | WO-2011/156578 | A1 | 12/2011 |
| WO | WO-2012/064910 | A1 | 5/2012 |
| WO | WO-2012/121758 | A1 | 9/2012 |
| WO | WO-2012/122279 | A1 | 9/2012 |
| WO | WO-2015/038736 | A2 | 3/2015 |
| WO | WO-2015/119848 | A1 | 8/2015 |
| WO | WO-2015/120014 | A1 | 8/2015 |
| WO | WO-2017/051385 | A1 | 3/2017 |
| WO | WO-2019/050759 | A1 | 3/2019 |
| WO | WO-2019/087161 | A1 | 5/2019 |
| WO | WO-2019/234709 | A1 | 12/2019 |
| WO | WO-2019/234710 | A1 | 12/2019 |
| WO | WO-2020/051137 | A1 | 3/2020 |
| WO | WO-2020/150703 | A1 | 7/2020 |
| WO | WO-2020/214906 | A1 | 10/2020 |
| WO | WO-2021/062282 | A1 | 4/2021 |
| WO | WO-2021/087210 | A1 | 5/2021 |
| WO | WO-2022/140537 | A1 | 6/2022 |
| WO | WO-2023/049920 | A1 | 3/2023 |
| WO | WO-2023/173005 | A2 | 9/2023 |
| WO | WO-2024/081718 | A1 | 4/2024 |

OTHER PUBLICATIONS

Allergan plc. (Nov. 5, 2015), "Allergan Outlines Open Science Model and Highlights Key Development Programs at R&D Day, Press Release." Retrieved from the Internet: http://www/multivu.com/players/English/7671931-allergan-r-d-day/, (Allergan plc, 2015), 5 pages.

Amerge (naratriptan hydrochloride) tablets, Highlights of Prescribing Information (2016).

American Headache Society (Jun. 9, 2016), Clinical Data Presented at American Headache Society Meeting Shows Promise of New Treatments for Migraine Prevention [Press Release]. Retrieved from the Internet: (https://americanheadachesociety.org/news/clinical-data-presented-at-american-headache-society-meeting-shows-promise-of-new-treatments-for-migraine-prevention/), 5 pages.

Anonymous., "Handbook of Pharmaceutical Excipients," 5th Edition, Pharmaceutical Press, 2006, 10 pages.

Anonymous., "Sample Preparation of Pharmaceutical Dosage Forms," Springer, 2011, 5 pages.

Anonymous: "Highlights of Prescribing Information: Qulipta", retreived online via <https://www.rxabbvie.com/pdf/qulipta_pi.pdf> (2021).

Anonymous: "Highlights of Prescribing Information: Ubrelvy (ubrogepant) tablets," retrieved online via <https://www.rxabbvie.com/pdf/ubrelvY-P i.pdf> (2021).

Ansel et al., "Pharmaceutical Dosage Forms and Drug Delivery Systems", 7th Edition, Lippincott Williams & Wilkins, 1999, pp. 367-369.

Armstrong., "Biohaven hopes to give Allergan a headache," Evaluate Vantage, retrieved online <https://www.evaluate.com/vantage/articles/interviews/biohaven-hopes-give-allergan-headache>: 3 pages (2018).

Arulmozhi et al., "Migraine: Current concepts and emerging therapies", Vascular Pharmacology, 43: 176-187 (2005).

Ashina et al. "Plasma levels of calcitonin gene-related peptide in chronic tension-type headache," Neurology 55.9: 1335-1340. (2000).

Awawdeh et al. "Quantitative analysis of substance P, neurokinin A and calcitonin gene related peptide in pulp tissue from painful and healthy human teeth," International endodontic Journal 35.1 : 30-36 (2002).

Bagley et al., "Validating Migraine-Specific Quality of Life Questionnaire v2.1 in Episodic and Chronic Migraine," Headache, Mar. 2012; vol. 5 2(3): pp. 409-421.

Barbanti et al., "The role of anti-CGRP antibodies in the pathophysiology of primary headaches," Neurol Sci 38 (Suppl. 1): pp. S31-S35 (2017).

Beer et al. "Systemic neuropeptide levels as predictive indicators for lethal outcome in patients with postoperative sepsis," Critical care medicine 30.8 : 1794-1798 (2002).

Belikov., "Pharmaceutical Chemistry," M. High School: 6 pages (1993).

(56) References Cited

OTHER PUBLICATIONS

Bell et al., MEDI 20: Discovery of AGN-241689: A potent, orally-acting CGRP receptor antagonist for migraine prophylaxis, 253 American Chemical Society, Abstracts, p. 20 (Apr. 2-6, 2017) (Year: 2017).
Bellamy et al. "Salivary levels of CGRP and VIP in rhinosinusitis and migraine patients," Headache: The Journal of Head and Face Pain 46.1: 24-33 (2006).
Bennet et al. "Alleviation of mechanical and thermal allodynia by CGRP8-37 in a rodent model of chronic central pain," Pain 86.1-2 : 163-175 (2000).
Bigal M.E., et al., "Body mass index and episodic headaches: a population-based study," Archives of internal medicine, Oct. 2007, vol. 167 (18), pp. 1964-1970.
Bigal M.E., et al., "Obesity and migraine: a population study," Neurology, 2006, vol. 66(4), pp. 545-550.
Boinpally et al., "63rd Annual Scientific Meeting American Headache Society: Evaluation of the pharmacokinetic interaction and safety of atogepant coadministered with esomeprazole magnesium", Headache 61 (S1): pp. 1-178 (2021).
Boinpally et al., "Single-Dose Pharmacokinetics and Safety of Atogepant in Adults With Hepatic Impairment: Results From an Open-Label, Phase 1 Trial," Clinical Pharmacology in Drug Development 10(7): pp. 726-733 (2021).
Boinpally et al., "Single-Dose Pharmacokinetics and Safety of Ubrogepant in Adults With Hepatic Impairment: Results From an Open-Label, Phase 1 Trial," Clinical Pharmacology in Drug Development, 0(0): 1-8 (2022).
Brauser, "Phase 3 Strive and Arise Trials Show Efficacy, Safety for Erenumab in Migraine Prevention," Medscape Medical News, 2017.
Burstein et al. "An association between migraine and cutaneous allodynia," Annals of neurology 47.5 614-624. (2000).
Cady et al. "Elevated saliva calcitonin gene-related peptide levels during acute migraine predict therapeutic response to rizatriptan," Headache: The Journal of Head and Face Pain 49.9: 1258-1266. (2009).
Cala M.L., et al., "The Activity Impairment in Migraine Diary (Aim-D): A novel migraine- specific patient-reported outcome measure to assess functioning based on activity impairment in episodic and chronic migraine patients", MTIS2018-005, Cephalalgia, 2018, vol. 38, pp. 1-115.
Chedid et al., "Hepatocellular Carcinoma: Diagnosis and Operative Management," ABCD Arq Bras Cir Dig 30(4): pp. 272-278 (2017).
Chen et al. "Menopausal flushes and calcitonin-gene-related peptide," The Lancet 342.8862 :p. 49.(1993).
Cheng et al. "The concentration of inhibitor which causes 50 percent inhibition (I) of an enzymatic reaction," Biochem. Pharmacol 22 : 3099-3108 (1973).
CHMP Guideline, "Guideline on the evaluation of the pharmacokinetics of medicinal products in patients with decreased renal function", European Medicines Agency, 15 pages, (2015).
Cho et al. "Development of Novel Fast-Dissolving Tacrolimus Solid Dispersion-Loaded Prolonged Release Tablet". European Journal of Pharmaceutical Sciences. Jan. 2014 [Online], 4:1-7. (Year: 2014).
Clinical Trial NCT02828020: Efficacy, Safety, and Tolerability Study of Oral Ubrogepant in the Acute Treatment of Migraine (Achieve I), https://clinicaltrials.gov/ct2/history/NCT02828020?V_1=View#StudyPageTop (2016).
Clinical Trial NCT02848326: Efficacy, Safety, and Tolerability of Multiple Dosing Regimens of Oral Atogepant (AGN-241689) in Episodic Migraine Prevention, https://clinicaltrials.gov/ct2/show/NCT02848326 (2016).
Clinical Trial NCT02867709: Efficacy, Safety, and Tolerability of Oral Ubrogepant in the Acute Treatment of Migraine (Achieve II), https://clinicaltrials.gov/ct2/show/results/NCT02867709 (2016).
Clinical Trial NCT03700320: Study to Evaluate the Safety and Tolerability of Treatment With Atogepant 60 mg Daily for the Prevention of Migraine in Participants With Episodic Migraine, https://clinicaltrials.gov/ct2/show/NCT03700320 (2018).
Clinical Trial NCT03777059: 12-Week Placebo-controlled Study of Atogepant for the Preventive Treatment of Migraine in Participants With Episodic Migraine, https://www.clinicaltrials.gov/ct2/show/NCT03777059 (2018).
Connor et al., "Randomized, controlled trial of telcagepant for the acute treatment of migraine", Neurology, 2009, pp. 970-977, 73.
Curto et al., "Ubrogepant for the treatment of migraine." Expert Opinion on Pharmacotherapy 21(7) (2020): 755-759.
Dahlof CGH. "Infrequent or non-response to oral sumatriptan does not predict response to other triptans—review of four trials," Cephalagia, Feb. 2006, vol. 26 (2), pp. 98-106.
Deen et al. "Blocking CGRP in migraine patients—a review of pros and cons," The Journal of Headache and Pain 18(96): 9 pages (2017).
Delay-Goyet et al. "Relative involvement oi substance P and CGRP mechanisms in antidromic vasodilation in the rat skin," Acta physiologica scandinavica 146.4 : 537-538.(1992).
Do et al., "Therapeutic novelties in migraine: new drugs, new hope?," The Journal of Headache and Pain, 20: Article 37 pp. 1-13 (2019).
Dodick et al., "Ubrogepant Achieves Onset of Pain Relief at 1 Hour for the Acute Treatment of Migraine (1223)", Neurology, 94(15), (2020).
Dodick et al., "Ubrogepant for the Acute Treatment of Migraine When Administered During the Prodrome (Premonitory Phase): Results From a Phase 3, Randomized, Double-blind, Placebo-Controlled, Crossover Study (S47. 001)." Neurology, (100)17 (2023).
Dodick et al., "Ubrogepant for the treatment of migraine", New England Journal of Medicine 381.23: 2230-2241 (2019).
Doods "Development of CGRP antagonists for the treatment of migraine," Current opinion in investigational Drugs 2.9: 1261-1268. (2001).
Doods et al. "Pharmacological profile of BIBN4096BS, the first selective small molecule CGRP antaaonist," British Journal of Pharmacology 29.3 : 420-423. (2000).
Dos Santos et al., "Small molecule CGRP receptor antagonists for the preventive treatment of migraine: a review." European Journal of Pharmacology 922 (2022): 174902.
Edvinsson et al. "Characterization of the effects of a non-peptide CGRP receptor antagonist in SK-N-MC cells and isolated human cerebral arteries," European journal of pharmacology 415. : 39-44. (2001).
Edvinsson et al., "Basic mechanisms of migraine and its acute treatment", Pharmacology and Therapeutics, 136: 319-333 (2012).
Edvinsson et al., "CGRP as the target of new migrainetherapies—successful translation from bench to clinic", Nature Reviews, 14: 338-350 (2018).
Edvinsson et al., "Neuropeptides in Migraine and Cluster Headache Review Article", Cephalalgia, Oct. 14, 1994 (Oct. 14, 1994), pp. 320-327, XP055542226.
Escott et al. "Trigeminal ganglion stimulation increases facial skin blood flow in the rat: a major role for calcitonin gene-related peptide," Brain research 669.i : 93-99 (1995).
Evans et al. "The asymmetric synthesis of. alpha.-amino acids. Electrophilic azidation of chiralimide enolates, a practical approach to the syntheses of (R) and (S)-alpha azido carboxylic acids," Journal of the American Chemical Society 112.10 : 4011-4030. (1990).
Extended European Search Report for EP Application No. 20869848.0 dated Dec. 22, 2023.
Fierce Biotech, "Merck kills Phill migraine drug program" (Jul. 29, 2011), available at <https://www.fiercebiotech.com/biotech/merck-kills-phiii-migraine-drug-program>.
Food and Drug Administration, "The Impact of Renal Impairment on Patient Drug Response Assessing the Need for a Consensus Approach", Pharmaceutical Science and Clinical Pharmacology Advisory Committee Meeting, (2019).
Foster et al. "Calcitonin gene-related peptide is chemotactic for human T lymphocytes," Annals of the New York Academy of Sciences 657.1 :397-404. (1992).
Friesen et al., "Hydroxypropyl Methylcellulose Acetate Succinate-Based Spray-Dried Dispersions: An Overview," Molecular Pharmaceutics, 5(6): 1003-1019 (2008).

(56) References Cited

OTHER PUBLICATIONS

Gelaye B., et al., "Body composition status and the risk of migraine: a meta-analysis," Neurology, May 2017, vol. 88 (19), pp. 1795-1804.
Gennaro Alfonso R., "Remington: The Science and Practice of Pharmacy", 2000, 20th edition, Table of Contents.
Global Health Metrics, "Global burden of 369 diseases and injuries in 204 countries and territories, 1990-2019: a systematic analysis for the Global Burden of Disease Study 2019", The Lancet, 396 (10258), pp. 1204-1222.
Goadsby et al. "Release of vasoactive peptides in the extracerebral circulation of humans and the cat during activation of the trigerninovascular system," Annals of Neurology: Official Journal of the American Neurological Association and the Child Neurology Society 23.2 : 193-196 (1988).
Goadsby et al. "Vasoactive peptide release in the extracerebral circulation of humans during migraine headache," Annals of Neurology: Official Journal of the American Neurological Association and the Child Neurology Society 28.2 183-187. (1990).
Goadsby et al., "Efficacy of Ubrogepant for the Treatment of Migraine Symptoms During the Prodrome (Premonitory Phase): Results From the Prodrome Trial" (2023)., Neurology, [Online] pp. 1-6.
Goadsby et al., "Safety and tolerability of ubrogepant following intermittent, high-frequency dosing: randomized, placebo-controlled trial in healthy adults." Cephalalgia 39.14 (2019): 1753-1761.
Goadsby et al., "Safety, tolerability, and efficacy of orally administered atogepant for the prevention of episodic migraine in adults: a double-blind, randomised phase 2b/3 trail" (2020).
Goadsby, "Bench to bedside advances in the 21st century for primary headache disorders: migraine treatments for migraine patients," Brain 139(10): pp. 2571-2577 (2016).
Goodman & Gilman's The Pharmacological Basis of Therapeutics, Joel G. Hardman et al., eds., McGraw-Hill Professional, 10th ed. 2001, Table of Contents.
Guo et al., "The Applications of Vitamin E TPGS in Drug Delivery," European Journal of Pharmaceutical Sciences, 49(2): 175-186 (2013).
Harmon et al. "Reaction of arylsulfonyl azides with N-methylindole, " The Journal of Organic Chemistry, 38.1, 11-16 (1973).
Herzog et al. "CGRP receptors in the gerbil spiral modular artery mediate a sustained vasodilation via a transient cAMP-mediated Ca2+-decrease," The Journal of membrane biology 189.3, 225-236. (2002).
Hewitt et al., "Randomized controlled trial of the CGRP receptor antagonist MK-3207 in the acute treatment of migraine," Cephalalgia Apr. 2011; 31(6): 712-22.
Ho et al., "Efficacy and Tolerability of MK-097 (telcagepant), a new oral antagonist of cacitonin gene-related peptide receptor, compared with zoimitriptant for acute migraine; a randomised, placebo-controlled parallel-treatment trial":, vol. 372,pp. 2115-2123, The Lancet, 2008, pp. 2115-2123, 372.
Ho et al., "Randomized Controlled trial of an oral CGRP receptor antagonist, MK-0974, in acute treatment of migraine", Neurology, Apr. 15, 2008; 70 (16): 1304-12.
Ho et al., "Randomized Controlled Trial of the CGRP receptor antagonist telcagepant for migraine prevention", Neurology, Sep. 9, 2014; 83(11): 958-66.
Ho et al., "Randomized controlled trial of the CGRP receptor antagonist telcagepant for prevention of headache in women with perimenstrual migraine", Cephalalgia, Feb. 2016;36(2): 148-61.
Hoffman et al. "Capsaicin-sensitive nerve fibers induce epithelial cell proliferation, inflammatory cell immigration and transforming growth factor-alpha expression in the rat colonic mucosa in vivo," Scandinavian Journal of Gastroenterology 37.4,414-422. (2002).
Holland P.R., and Goadsby P.J., "Targeted CGRP Small Molecule Antagonists for Acute Migraine Therapy," Neurotherapeutics, Apr. 2018, vol. 15 (2), pp. 304-312.
Holzer et al. "Job queues and wages," Title Quarterly Journal of Economics 106.3, 739-768. (1991):.
Holzer et al., "Evaluation o Sodium Stearyl Fumarate as a Tablet Lubricant," International Journal of Pharmaceutics, 2(3-4): 145-153 (Abstract Only)(1979).
Hutchinson et al., "Ubrogepant for the Acute Treatment of Migraine: Pooled Safety and Tolerability From Achieve I and Achieve Ii Phase 3 Studies (117)", Neurology, 94(15), (2020).
IMITREX (sumatriptan) tablets, Highlights of Prescribing Information (2020).
International Preliminary Report on Patentability for International Application No. PCT/IB19/54780 dated Dec. 8, 2020.
International Preliminary Report on Patentability for International Application No. PCT/US15/13672 dated Aug. 9, 2016.
International Preliminary Report on Patentability for International Application No. PCT/US20/28666 dated Oct. 28, 2021.
International Preliminary Report on Patentability for International Application No. PCT/US21/43791 dated Nov. 18, 2021.
International Search Report and Written Opinion for International Application No. PCT/US23/76576 dated Feb. 23, 2024.
International Search Report and Written Opinion for International Application No. PCT/IB19/54780, dated Oct. 28, 2019.
International Search Report and Written Opinion for International Application No. PCT/IB19/54781 dated Oct. 22, 2019.
International Search Report and Written Opinion for International Application No. PCT/US11/60081, dated Dec. 19, 2011.
International Search Report and Written Opinion for International Application No. PCT/US15/13672 dated Apr. 21, 2015.
International Search Report and Written Opinion for International Application No. PCT/US20/28666 dated Aug. 28, 2020.
International Search Report and Written Opinion for International Application No. PCT/US20/52891 dated Feb. 17, 2021.
International Search Report and Written Opinion for International Application No. PCT/US21/64853 dated Mar. 18, 2022.
International Search Report and Written Opinion for International Application No. PCT/US22/77061 dated Jan. 4, 2023.
International Search Report and Written Opinion for International Application No. PCT/US23/64027 dated Sep. 26, 2023.
Israel et al., "CGRP Monoclonal Antibodies for the Preventative Treatment of Migraine," Current Pain and Headache Reports 22.5 (2018): 1-6.
Jakate et al., "Effects of CYP3A4 and P-glycoprotein inhibition or induction on the pharmacokinetics of ubrogepant in healthy adults: Two phase 1, open-label, fixed-sequence, single-center, crossover trials," Cephalalgia Reports, 4: 1-10 (2021).
Johnson et al., "A pharmacogenomic evaluation of migraine therapy", Expert Opinion on Pharmacotherapy, 8: 1821-1835 (2007).
Kasarala G. et al., "Standard Liver Tests," Clinical Liver Disease, Jul. 2016, vol. 8 (1), pp. 13-18.
Kibbe, "Handbook of Pharmaceuticals Excipients", 2000, Pharmaceutical Press, XP002773202, p. 386.
Kielbasa et al., "A new era for migraine: pharmacokinetic and pharmacodynamic insights into monoclonal antibodies with a focus on galcanezumab, an anti-CGRP antibody", Cephalalgia 39.10: 1284-1297 (2019).
Kopruszinski et al., "Prevention of stress- or nitric oxide donor-induced medication overuse headache by a calcitonin gene-related peptide antibody in rodents," Cephalalgia, 37(6): 560-570 (2017).
Kristoffersen E.S., et al., "Migraine, Obesity, and Body Fat Distribution—a Population-Based Study," The journal of headache and pain, Aug. 2020, vol. 21 (1), pp. 97.
Lance "Headache Pathogenesis: Monoarnines," Neuropeptides, Purines & Nitric Oxide 3-9 (1997).
Lars Edvinsson: "CGRP as the target of new migraine therapies—successful translation from bench to clinic", Nature Reviews, Apr. 24, 2018 (Apr. 24, 2018). XP055476796.
Lassen et al. "CGRP may play a causative role in migraine," Cephalalgia 22.1 (2002): 54-61.
Late-Breaking Abstracts: 60th Annual Scientific Meeting, American Headache Society, 60th Annual Scientific Meeting American Headache Society, AHS 2018. San Francisco, CA, United States. Jun. 28-Jul. 1, 2018.
Li et al. "Effect of CGRP receptor antagonist CGRP8-37 on nociceptive response, NOS expression and NO content in the dorsal

(56) References Cited

OTHER PUBLICATIONS horn of spinal cord during formalin-induced inflammatory pain in rats," Chinese Journal of Applied Physiology. 20(3): 291-295. (2004).
Lipton et al., "Effect of ubrogepant vs placebo on pain and the most bothersome associated symptom in the acute treatment of migraine: the Achieve II randomized clinical trial." Jama 322.19: 1887-1898 (2019).
Lipton et al., "Efficacy, safety, and tolerability of rimegepant 75 mg orally dissolving tablet for the acute treatment of migraine: Results from a phase 3, double-blind, randomized, placebo- controlled trial, Study 303", Headache, 59: 21-22 (2019).
Lipton et al., (Postgraduate Medicine, Minneapolis (2001) 109: 1-6)(2001).
Lipton R.B, et al., "Impact of NSAID and Triptan Use on Developing Chronic Migraine: Results from the American Migraine Prevalence and Prevention (AMPP) Study," Headache, Nov./Dec. 2013, vol. 53 (10), pp. 1548-1563.
Magellan RX Management, Ubrogepant (Ubrelvy™) New Drug Update; retrieved online <https://www.hhs.texas.gov/sites/default/files/documents/about-hhs/communications-events/meetings-events/dur/may-2020/may-2020-durb-agenda-item-5c.pdf>: 8 pages (2020).
May et al. "Intractable eye pain: indication for triotans," Cephalalgia 22.3, 195-196.(2002).
McCarthy, "Oral rimegepant increased freedom from pain and from most bothersome symptom at 2 h in acute migraine." Annals of internal medicine 171(10) (2019): JC59.
Medsafe, "Drug Metabolism—The Importance of Cytochrome P450 3A4", retrieved online https://www.medsafe.govt.nz/profs/PUArticles/March2014DrugMetabolismCytochromeP4503A 4.htm (2014).
Meglio, "Dose-Dependent Weight Reductions Observed With Atogepant", Neurology Live, Jun. 15, 2022.
Menard et al. "A calcitonin gene-related peptide receptor antagonist prevents the development of tolerance to spinal morphine analgesia," Journal of Neuroscience 16. 7, 2342-2351 (1996).
Merck, B.I. and Co Inc Harleysville PA USA et al: "Discovery of AGN-241689: A potent, orally-acting CGRP receptor antagonist for migraine prophylaxis", Abstracts of Papers, ACS National Meeting & Exposition; 253rd National Meeting Of The American-Chemical-Society (ACS) On Advanced Materials, Technologies, Systems, And Processes; San Francisco, CA, USA, Apr. 2-6, 2017. American Chemical Society, vol. 253. Apr. 2, 2017 (Apr. 2, 2017). p. 20. XP009516497.
Messali A.J., et al., "Treatment persistence and switching in triptan users: a systematic literature review," Headache, Jul.-Aug. 2014, vol. 54 (7), pp. 1120-1130.
Messina R., et al., "CGRP—A Target for Acute Therapy in Migraine: Clinical Data," Cephalalgia, An International Journal of Headache, 2019, vol. 39(3), pp. 420-427.
Molina et al. "Induction of Insulin Resistance In Vivo by Amylin and Calcitonin Gene—Related Peptide," Diabetes 39.2, 260-265 (1990).
Mullin et al., "Potential for treatment benefit of small molecule CGRP receptor antagonist plus monoclonal antibody in migraine therapy", Neurology, vol. 94, No. 20, Jan. 13, 2020, pp. e2121-e2125.
Mullin, "Acute treatment benefit from oral CGRP receptor antagonist and monoclonal antibody combination: rimegepant 75mg for acute treatment of attacks during preventive therapy with erenumab", 61st Annual Scientific Meeting American Headache Society, Jun. 1, 2019, pp. 176-177.
Mullin, "Successful gepant-monoclonal antibody combination: Rimegepant 75mg for acute treatment of attacks during preventive therapy with erenumab", Cephalalgia Sep. 1, 2019 Sage Publications Ltd NLD, vol. 39, No. 1, Supplement, Sep. 1, 2019.
National Center for Biotechnology Information ""*Homo sapiens* mRNA encoding RAMP1,"" GenBank Accession No. AJ001014, 2 pages, (2008).
National Center for Biotechnology Information "*Homo sapiens* (clone HSNME29) CGRP type 1 receptor mRNA, complete ends," GenBank Accession No. L76380,2 pages, (1996).
Negro A., et al., "CGRP Receptor Antagonists: An Expanding Drug Class for Acute Migraine?," Expert Opinion on Investigational Drugs, 2012, vol. 21(6), pp. 807-818.
Negro A., et al., "Serotonin receptor agonists in the acute treatment of migraine: a review on their therapeutic potential," Journal of Pain Research, Mar. 2018, vol. 11, pp. 515-526.
Negro et al., "Gepants for the treatment of migraine," Expert Opinion on Investigational Drugs 28.6 (2019): 555-567.
Neuschwander-Tetri B.A et al., "The upper limits of normal for serum ALT levels reported by clinical laboratories depend on local reference populations," Arch Intern Med., Mar. 2004, vol. 168(6), pp. 663-666.
Olesen et al. "Calcitonin gene-related peptide receptor antagonist BIBN 4096 BS for the acute treatment of migraine," New England Journal of Medicine 350.11, 1104-1110. (2004).
Ornello R., et al., "Migraine and body mass index categories: a systematic review and meta-analysis of observational studies," The journal of headache and pain, Mar. 2015, vol. 16 (1), 14 pgs.
Partial EP Search Report for EP Application No. 20869848.0 dated Sep. 21, 2023.
Peterlin B.L., et al., "Obesity and migraine: the effect of age, gender and adipose tissue distribution," Headache, Jan. 2010, vol. 50 (1), pp. 52-62.
Petersen et al. "BIBN4096BS Antagonizes Human a-calcitonin Gene Related Peptide-C35 induced Headache and Extracerebral Artery Dilatation," Clinical Pharmacology & Therapeutics 77.3 :202-213.(2005).
Pitt et al., "Determination of the Tensile Strength of Elongated Tablets," Powder Technology, 238: 169-175 (2013).
Ramadhani et al. "Preparation and Characterisation of Kolliphor p. 188 and p. 237 Solid Dispersion Oral Tablets Containing the Poorly Water Soluble DrugDisulfiram". International Journal of Pharmaceutics. Sep. 2014 [Online], 475:514-522. (Year: 2014).
Rapoport et al., "Triptans are all Different", Arch Neurol, 58(9):1479-1480 (2001).
Remington J.P "Remington's Pharmaceutical Sciences," 17th Edition Edited by Alfonso R. Gennaro, Mack Publishing Co, Journal of Pharmaceutical Science, 1985, vol. 74 (10).
Remington, "The Science and Practice of Pharmacy", 2000, Lippincott Williams&Wilkins, XP002773203, pp. 861-862.
Repka et al., "Melt Extrusion: Process to Product," Expert Opinion on Durg Delivery, Dec. 6, 2011, 9(1): 105-125.
Reuter, "A Review of Monoclonal Antibody Therapies and Other Preventative Treatments in Migraine", Headache, Woodbury, NJ, United States, vol. 58, Apr. 26, 2018, pp. 48-59.
Rohrenbeck et al. "Upregulation of COX-2 and CGRP expression in resident cells of the C36 Borna disease virus-infected brain is dependent upon inflammation," Neurobiology of disease 6.1 : 15-34.(1999).
Rowe et al., "Handbook of Pharmaceutical Excipients", 2000, Pharmaceutical Press, XP002773225, p. 201.
Rowe R.C., et al., "Handbook of Pharmaceutical Excipients," APhA Publications, 4th edition, 2003. pp. 1-6.
Russo., "CGRP-Based Migraine Therapeutics: How Might They Work, Why So Safe, and What Next?," ACS Pharmacology & Translational Science, 2(1): 2-8 (2019).
Salmon et al. "Altered neuroadaptation in opiate dependence and neurogenic inflammatory nociceotion in aCGRP-deficient mice," Nature neuroscience 4.4, : 357-358. (2001).
Saunders , B., "Allergan 2015 R&D Day", (Nov. 5, 2015), Powerpoint Presentation, slide 1-3 and 49-51. (Allergan plc, 2015).
Scher A.I., et al., "Factors associated with the onset and remission of chronic daily headache in a population-based study," Pain, Nov. 2003, vol. 106 (1-2), pp. 81-89.
Schini-Kerth et al. "CGRP enhances induction of NO synthase in vascular smooth muscle C38 cells via a CAMP—dependent mechanism," American Journal of Physiology—Heart and Circulatory Physiology 267.6 : 2483 -2490 (1994).

(56) References Cited

OTHER PUBLICATIONS

Schuster et al., "Calcitonin Gene-Related Peptide-Targeted Therapies for Migraine and Cluster Headache: A Review," Clinical Neuropharmacology, 40(4): 169-174 (2017).
Schwedt et al., "Time course efficacy of atogepant for the preventive treatment of migraine: Results from the randomized, double-blind Advance trial" Cephalgia, vol. 42, No. 1, p. 3-11 (2022).
Scott., "Ubrogepant: First Approval," Drugs, 80: 323-328 (2020).
Serrano D., et al., "Effects of Switching Acute Treatment on Disability in Migraine Patients Using Triptans," Headache, Oct. 2013, vol. 53 (9), pp. 1415-1429.
Shaw et al., "Carprolactams as Potent CGRP Receptor Antagonists for the Treatment of Migraine", Bioorg Med. Chem Lett, 2007, pp. 4795-4798, 17.
Silberstein S.D., et al., "Pharmacologic treatment for episodic migraine prevention in adult," American Academy of Neurology, Apr. 2012, vol. 78 (17), pp. 1337-1345.
Spetz et al. "Momentary increase in plasma calcitonin gene-related peptide is involved in hot flashes in men treated with castration for carcinoma of the prostate," The Journal of urology 166.5, 1720-1723.(2001).
Supplementary European Search Report for EP Application No. 21850713.5 dated Jun. 26, 2024.
Szkutnik-Fiedler et al., "Pharmacokinetics, Pharmacodynamics and Drug-Drug Interactions of New Anti-Migraine Drugs-Lasmiditan, Gepants, and Calcitonin-Gene-Related Peptide (CGRP) Receptor Monoclonal Antibodies," Pharmaceutics, 12(12): 1-22 (2020).
Talal et al., "Assessment of hepatic impairment and implications for pharmacokinetics of substance use treatment", Clinical pharmacology in drug development 6.2: 206-212 (2017).
Tepper et al., "Erenumab in chronic migraine with medication overuse" Neurology, 92(20): e2309-2320 (2019).
Tepper et al., "Safety and efficacy of erenumab for preventive treatment of chronic migraine: a randomised, double-blind, placebo-controlled phase 2 trial," The Lancet Neurology, 16(6): 425-434 (2017).
Tepper, "Anti-Calcitonin Gene-Related Peptide (CGRP) Therapies: Update on a Previous Review After the American Headache Society 60th Scientific Meeting, San Francisco, Jun. 11, 2018," Headache 58.7 (2018): 276-290.
Tepper, "CGRP and headache: a brief review", Neurological Sciences (Testo Stampato), Springer Verlag, Milan, IT, vol. 40, No. 1, Mar. 5, 2019, pp. 99-105.
Viana M., et al., "Triptan non-responders: do they exist and who are they?," Cephalalgia, Aug. 2013, vol. 33 (11 ), pp. 891-896.
Voss et al., "A phase IIb randomized, double-blind, placebo-controlled trial of ubrogepant for the acute treatment of migraine," Cephalalgia, 36(9): 887-898 (2016).
Walker et al. "Mice lacking the neuropeptide a-calcitonin gene-related peptide are protected against diet-induced obesity," Endocrinology 151.9 : 4257-4269. (2010).
Wallengren "Dual effects of CGRP-antagonist on allergic contact dermatitis in human skin." Contact dermatitis 43.3, : •137-143 (2000).
Williamson et al. ""The CGRP Family: Calcitonin Gene-Related Peptide (CGRP), Amylin, and Adrenomedullin, Landes,"" Bioscience 245-247.(2000).
Williamson et al. "Sumatriptan inhibits neurogenic vasodilation of dural blood vessels in the anaesthetized rat-intravital microscope studies," Cephalalaia 17.4 : 525-531 (1997).
Winter A.C. "Body mass index, migraine, migraine frequency and migraine features in women," Cephalalgia, Feb. 2009, vol. 29(2), pp. 269-278.
Wu et al., "Regulatory perspectives of Type II prodrug development and time-dependent toxicity management: Nonclinical Pharm/Tox analysis and the role of comparative toxicology," Toxicology 236(1-2): pp. 1-6 (2007).
Yang M., et al., "Validation of the Headache Impact Test (HIT-6™) Across Episodic and Chronic Migraine," Cephalalgia, Feb. 2011; vol. 31(3), pp. 357-367.
Yoshida et al. "Systematic and quantitative assessment of the effect of chronic kidney disease on CYP2D6 and CYP3A4/5." Clinical Pharmacology & Therapeutics 100.1 (2016): 75-87.
Yu et al. "Effects of calcitonin gene-related peptide-(8-37) on withdrawal responses in rats with inflammation," European journal of pharmacology 347.2-3, 275-282. (1998).
Yuan et al., "CGRP therapeutics for the treatment of migraine—a narrative review." Ann Head Med 1 (2020): 1-22.
Zhang et al. "Arthritic calcitonin/a calcitonin gene-related peptide knockout mice have reduced nociceptive hypersensitivity," Pain 89.2-3,: 265-273. (2001).
Zheng et al. "Severity of neurological signs and degree of inflammatory lesions in the brains of rats with Borna disease correlate with the induction of nitric oxide synthase," Journal of Virology 67.10, 5786-5791. (1993).
Boinpally et al., "Evaluation of the Pharmacokinetic Interaction and Safety of Coadministered Atogepant and Topiramate," Cephalalgia, vol. 41, No. 1 (Supplemental), pp. 267-268, Abstract No. P0474 (2021).
Alberici et al., "Topiramate weight loss in migraine patients." Journal of the Neurological Sciences 278.1-2 (2009): 64-65.
Ankrom et al., "Atogepant Has No Clinically Relevant Effects on the Pharmacokinetics of an Ethyl Estradiol/Levonorgestrel Oral Contraceptive in Healthy Female Participants", The Journal of Clinical Pharmacology, vol. 60, No. 9, pp. 1157-1165 (2020).
Bell, "Calcitonin gene-related peptide receptor antagonists: new therapeutic agents for migraine." Journal of Medicinal Chemistry 57(19) (2014): 7838-7858.
Bond et al., "Migraine and obesity: epidemiology, possible mechanisms and the potential role of weight loss treatment." Obesity Reviews 12 (2011): e362-e371.
Deng et al., "Efficacy and safety of calcitonin-gene-related peptide binding monoclonal antibodies for the preventive treatment of episodic migraine-an updated systematic review and meta-analysis." BMC Neurology 20 (2020): 57.
Dodick et al., "Responder Rates to Atogepant in Patients with Episodic Migraine: A Post Hoc Analysis of Results from a Phase 2b/3, Randomized, Double-Blind, Placebo-Controlled Trial." American Headache Society 61st Annual Scientific Meeting, P87 (Jul. 2019).
Dresser et al., "Pharmacokinetic-pharmacodynamic consequences and clinical relevance of cytochrome P450 3A4 inhibition." Clinical Pharmacokinetics 38 (2000): 41-57.
Edvinsson, "CGRP receptor antagonists and antibodies against CGRP and its receptor in migraine treatment." British Journal of Clinical Pharmacology 80(2) (2015): 193-199.
Fahmi et al., "Comparison of different algorithms for predicting clinical drug—drug interactions, based on the use of CYP3A4 in vitro data: predictions of compounds as precipitants of interaction." Drug Metabolism and Disposition 37(8) (2009): 1658-1666.
Goadsby et al., "Orally Administered Atogepant Was Efficacious, Safe, and Tolerable for the Prevention of Migraine: Results From a Phase 2b/3 Study", Neurology, vol. 92, No. Supplement 15, p. S17.001 (Apr. 9, 2019).
Goadsby et al., "Pathophysiology of migraine: a disorder of sensory processing." Physiological Reviews 97 (2017): 553-622.
Li et al., "Characterizing the PK/PD relationship for inhibition of capsaicin-induced dermal vasodilatation by MK-3207, an oral calcitonin gene related peptide receptor antagonist." British Journal of Clinical Pharmacology 79(5) (2015): 831-837.
Taylor, "Weight change associated with the use of migraine-preventive medications." Clinical Therapeutics 30(6) (2008): 1069-1080.

* cited by examiner

Treatment A: Single 60 mg dose of Atogepant on Day 1
Treatment B1: Itraconazole 200 mg once daily on days 8 to 14
Treatment B2: Itraconazole 200 mg coadministered with 60 mg atogepant on Day 15, followed by Itraconazole 200 mg on Days 16-17

Treatment A: Single 60 mg dose of Atogepant on Day 1
Treatment B1: Itraconazole 200 mg once daily on days 8 to 14
Treatment B2: Itraconazole 200 mg coadministered with 60 mg atogepant on Day 15, followed by Itraconazole 200 mg on Days 16-17

Change from Baseline in Monthly Migraine Days in Study 1

Distribution of Change from Baseline in Mean Monthly Migraine Days by Treatment Group in Study 1

Change from baseline in Monthly Migraine Days in Study 2

Distribution of Change from Baseline in Mean Monthly Migraine Days by Treatment Group in Study 2

Mean ± SD Plasma Atogepant Concentration (ng/mL) – Time Profile, Linear Scale – (PK Population) [inset – Mean profile, semilogarithmic scale]

Mean (±SD) steady state plasma atogepant concentrations when administered alone and in combination with topiramate Linear Scale Semi-logarithmic Scale Mean (±SD) steady state plasma topiramate concentrations when administered alone and in combination with atogepant.

Linear Scale

Semi-logarithmic Scale

METHODS OF TREATING MIGRAINE

CROSS-REFERENCE TO RELATED APPLICATIONS

This application is a divisional of U.S. application Ser. No. 17/953,536, filed Sep. 27, 2022; which claims the benefit of priority to U.S. Provisional Application No. 63/261,731, filed Sep. 27, 2021; U.S. Provisional Application No. 63/261,782, filed Sep. 28, 2021; U.S. Provisional Application No. 63/261,783, filed Sep. 28, 2021; U.S. Provisional Application No. 63/336,843, filed Apr. 29, 2022; and U.S. Provisional Application No. 63/395,134, filed Aug. 4, 2022. The entire contents of each of these applications is incorporated herein by reference in its entirety.

FIELD

The present disclosure is related to medicaments and methods for treating migraine.

BACKGROUND

Migraine is a highly prevalent, severe, and disabling neurological condition with a significant unmet need for effective treatments. (Holland, P. R. & Goadsby, P. J. Neurotherapeutics (2018). Migraine affects over 1 billion people worldwide, and it was reported as the second leading cause of disability in the 2016 Global Burden of Discase study. See GBD 2019 Diseases and Injuries Collaborators. Global Burden of 369 diseases and injuries in 204 countries and territories, 1990-2019: a systemic analysis for the Global Burden of Disease Study 2019, Lancet 2020; 396:1204-22.

When attacks are frequent or disabling, prevention becomes a focus of migraine treatment. Current preventive treatments for migraine include oral medications, such as valproic acid, flunarizine, topiramate, and propranolol, as well as injectable treatments, such as monoclonal antibodies targeting calcitonin gene-related peptide (CGRP).

There remains a need for targeted methodologies and dosing regimens to use oral CGRP treatments to prophylactically treat migraines.

SUMMARY

In embodiments, the present disclosure provides methods for the preventive treatment of migraine in a patient, wherein the patient is undergoing concurrent treatment with a strong CYP3A4 inhibitor, the method comprising administering atogepant 10 mg once daily.

In embodiments, the present disclosure provides methods for the preventive treatment of migraine in a patient, wherein the patient is undergoing concurrent treatment with a moderate or strong CYP3A4 inducer, the method comprising administering 30 mg or 60 mg atogepant once daily.

In embodiments, the present disclosure provides methods for the preventive treatment of migraine in a patient, wherein the patient is undergoing concurrent treatment with an OATP inhibitor, the method comprising administering 10 mg or 30 mg atogepant once daily.

In embodiments, the present disclosure provides methods for the preventive treatment of migraine in a patient, wherein the patient has severe renal impairment or end-stage renal disease (CLcr<30 mL/min), the method comprising administering 10 mg atogepant once daily.

BRIEF DESCRIPTION OF THE FIGURES

FIG. 5A presents a full profile up to 72 hours, while 5B shows a truncated profile up to 8 hours.

DETAILED DESCRIPTION

Figure 1:
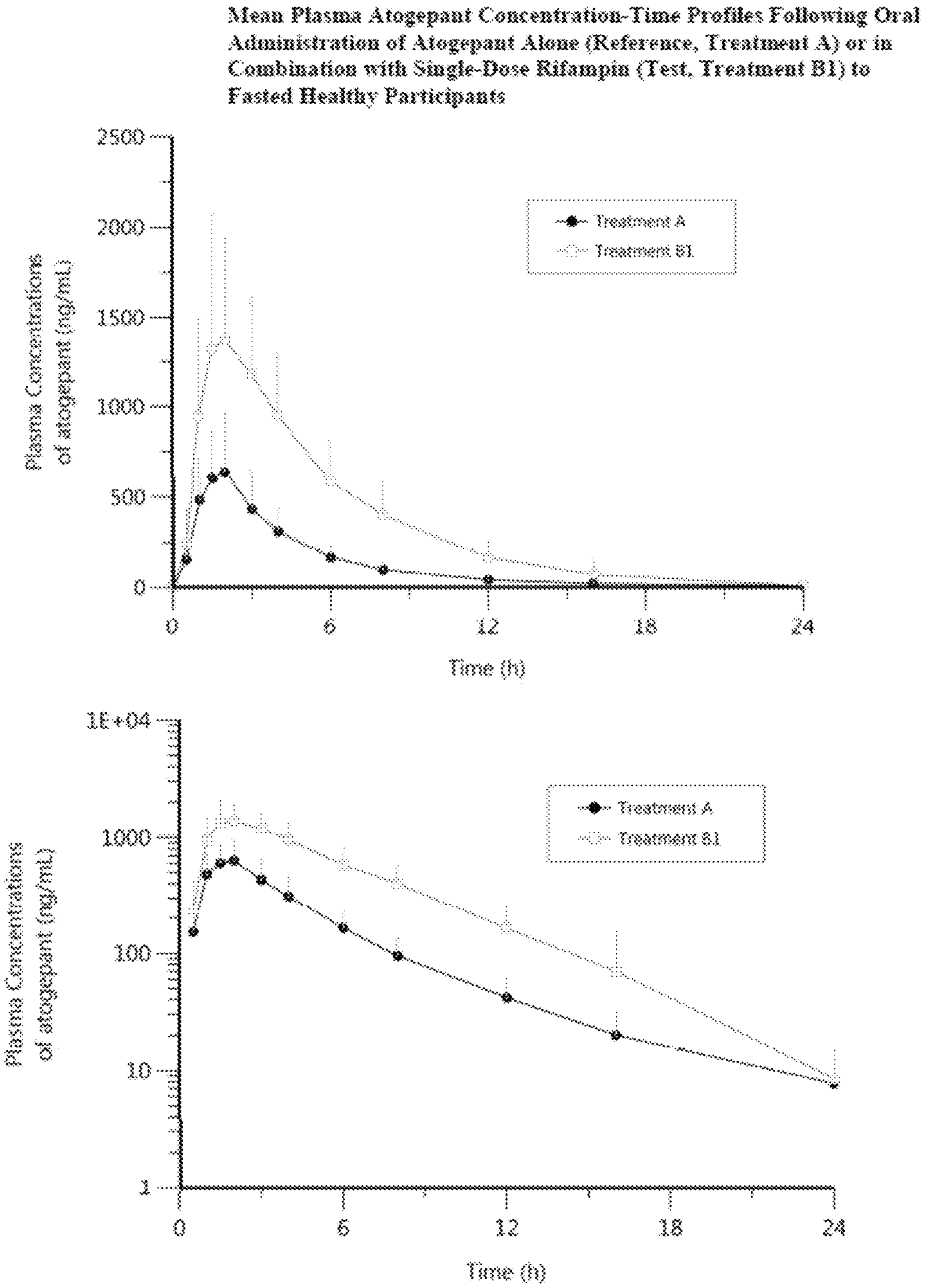
FIG. 1 shows the mean plasma atogepant concentration-time profiles following administration of atogepant alone or in combination with single-dose rifampin to Fasted Healthy Participants.

The present disclosure provides methods for treating migraine in a patient in need thereof. In embodiments, the present disclosure provides methods for the prophylactic treatment of patients suffering from migraine. In embodiments, the present disclosure provides methods for the preventive treatment of episodic migraine. In embodiments, the present disclosure provides methods for the treatment of migraine, such as the preventive treatment of episodic migraine, comprising administering a prophylactically effective amount of atogepant or a pharmaceutically acceptable salt thereof. The chemical name of atogepant is (3'S)—N-[(3S,5S,6R)-6-methyl-2-oxo-1-(2,2,2-trifluoroethyl)-5-(2,3,6-trifluorophenyl) piperidin-3-yl]-2'-oxo-1',2',5,7-tetrahydrospiro[cyclopenta[b]pyridine-6,3'-pyrrolo[2,3-b]pyridine]-3-carboxamide, and it has the following structural formula:

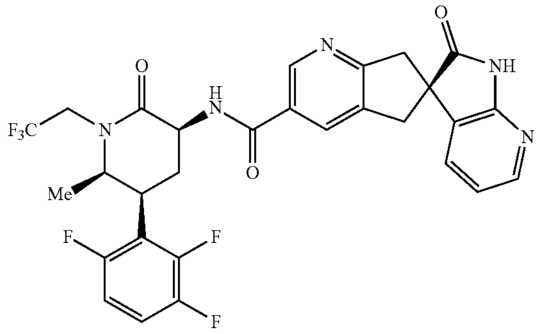

Atogepant

Atogepant is a small molecule calcitonin gene-related peptide (CGRP) receptor antagonist which may be administered orally as, for example, a tablet. In embodiments, atogepant is administered for the preventive treatment of migraine, such as episodic migraine. In embodiments, atogepant is administered for the preventive treatment of episodic migraine at a once daily dose of 10 mg, 30 mg, or 60 mg.

Following oral administration, atogepant is absorbed with peak plasma concentrations at approximately 1 to 2 hours. Following once daily dosing, atogepant displays dose-proportional pharmacokinetics up to 170 mg, with no accumulation.

When atogepant is administered with a high-fat meal, the food effect was not significant (AUC and $C_{max}$ were reduced by approximately 18% and 22%, respectively, with no effect on median time to maximum atogepant plasma concentration). In embodiments, atogepant may be administered without regard to food.

Plasma protein binding of atogepant was not concentration-dependent in the range of 0.1 to 10 μM; the unbound fraction of atogepant was approximately 4.7% in human plasma. The mean apparent volume distribution of atogepant (Vz/F) after oral administration is approximately 282 L.

Atogepant is eliminated mainly through metabolism, primarily by CYP3A4. The parent compound (atogepant) and a glucuronide conjugate metabolite (M23) were the most prevalent circulating components in human plasma. The elimination half-life of atogepant is approximately 11 hours. The mean apparent oral clearance (CL/F) of atogepant is approximately 19 L/hr. Following a single oral dose of 50 mg $^{14}C$-atogepant to healthy male subjects, 42% and 5% of the dose was recovered as unchanged atogepant in feces and urine, respectively.

In vitro, atogepant is not an inhibitor for CYPs 3A4, 1A2, 2B6, 2C8, 2C9, 2C19, or 2D6 at clinically relevant concentrations. Atogepant does not inhibit MAO-A or UGT1A1 at clinically relevant concentrations. Atogepant is not an inducer of CYP1A2, CYP2B6, or CYP3A4 at clinically relevant concentrations.

Atogepant is a substrate of P-gp, BCRP, OATP1B1, OATP1B3, and OAT1. Atogepant is not an inhibitor of P-gp, BCRP, OAT1, OAT3, NTCP, BSEP, MRP3, or MRP4 at clinically relevant concentrations. Atogepant is a weak inhibitor of OATP1B1, OATP1B3, OCT1, and MATE1.

The terms "concurrent"/"concurrently" or "concomitant"/"concomitantly" both include in their meaning (1) simultaneously in time (e.g., at the same time) and (2) at different times but within the course of a common treatment schedule.

Coadministration of Atogepant and a CYP3A4 Inhibitor

Coadministration of atogepant with itraconazole, a strong CYP3A4 inhibitor, resulted in a significant increase in exposure of atogepant in healthy subjects. Co-administration of atogepant with itraconazole resulted in a clinically significant increase (Cmax by 2.15-fold and AUC by 5.5-fold) in the exposure of atogepant in healthy subjects. Population pharmacokinetic modeling suggested co-administration of atogepant with moderate CYP3A4 inhibitors (e.g., cyclosporine, ciprofloxacin, fluconazole, fluvoxamine, grapefruit juice) or weak CYP3A4 inhibitors (e.g., cimetidine, esomeprazole) increase atogepant AUC by 1.7- and 1.1-fold, respectively. The changes in atogepant exposure when coadministered with weak or moderate CYP3A4 inhibitors are not expected to be clinically significant.

In embodiments, the present disclosure provides methods for the preventive treatment of migraine, such as the preventive treatment of episodic migraine, when atogepant is used concomitantly with a strong CYP3A4 inhibitor (e.g., ketoconazole, itraconazole, clarithromycin).

In embodiments, the present disclosure provides a method for the preventive treatment of migraine (such as the preventive treatment of episodic migraine) in a patient undergoing concurrent treatment with a strong CYP3A4 inhibitor, the method comprising administering 10 mg atogepant once daily. In embodiments, the CYP3A4 inhibitor is ketoconazole, itraconazole, or clarithromycin. In embodiments, coadministration of 10 mg atogepant and the strong CYP3A4 inhibitor results in an increase in atogepant Cmax of less than 2.15-fold relative to administration of atogepant alone. In embodiments, coadministration of 10 mg atogepant and the strong CYP3A4 inhibitor (e.g., itraconazole) results in an increase in atogepant AUC of less than or equal to 5.5-fold relative to administration of atogepant alone. In embodiments, atogepant is administered with or without food. In embodiments, the CYP3A4 inhibitor may be administered before, concomitantly with, or after atogepant is administered.

In embodiments, the present disclosure provides a method for the preventive treatment of migraine (such as the preventive treatment of episodic migraine) in a patient, the method comprising administering 10 mg or 30 mg or 60 mg of atogepant once daily, wherein if the patient begins concurrent treatment with a strong CYP3A4 inhibitor, the dose of atogepant is adjusted to 10 mg once daily. In embodiments, the CYP3A4 inhibitor may be administered before, concomitantly with, or after atogepant is administered.

In embodiments, the present disclosure provides a method for the preventive treatment of migraine (such as the preventive treatment of episodic migraine) in a patient undergoing concurrent treatment with a moderate CYP3A4 inhibitor, the method comprising administering 10 mg, 30 mg, or 60 mg atogepant once daily. In embodiments, the moderate CYP3A4 inhibitor is cyclosporine, ciprofloxacin, fluconazole, fluvoxamine, and grapefruit juice. In embodiments, coadministration of atogepant and the moderate CYP3A4 inhibitor increases atogepant AUC by about 1.7-fold or less, relative to administration of atogepant alone. In embodiments, atogepant is administered orally with or without food. In embodiments, the CYP3A4 inhibitor may be administered before, concomitantly with, or after atogepant is administered.

In embodiments, the present disclosure provides a method for the preventive treatment of migraine (such as the preventive treatment of episodic migraine) in a patient undergoing concurrent treatment with a weak CYP3A4 inhibitor, the method comprising administering 10 mg, 30 mg, or 60 mg atogepant. In embodiments, the mild CYP3A4 inhibitor is cimetidine or esomeprazole. In embodiments, coadministration of 10 mg, 30 mg, or 60 mg atogepant and the weak CYP3A4 inhibitor increases AUC by about 1.1-fold or less, relative to administration of atogepant alone. In embodiments, atogepant is administered orally with or without food. In embodiments, the CYP3A4 inhibitor may be administered before, concomitantly with, or after atogepant is administered.

Coadministration of Atogepant and a CYP3A4 Inducer

Co-administration of atogepant with rifampin, a strong CYP3A4 inducer, decreased atogepant AUC by 60% and Cmax by 30% in healthy subjects. Moderate inducers of CYP3A4 can decrease atogepant exposure.

In embodiments, the present disclosure provides a method for the preventive treatment of migraine (such as the preventive treatment of episodic migraine) in a patient undergoing concurrent treatment with a strong or moderate CYP3A4 inducer, the method comprising administering 30 mg or 60 mg atogepant. In embodiments, the strong CYP3A4 inducer is rifampin, carbamazepine, phenytoin, St. John's wort, efavirenz, or etravirine. In embodiments, atogepant is administered with the CYP3A4 inducer has reached a steady state. In embodiments, the AUC of atogepant is decreased by less than about 60% when 30 mg or 60 mg atogepant is administered with the moderate or strong CYP3A4 inducer relative to administration of atogepant alone. In embodiments, the atogepant Cmax is decreased by less than about 30% when co-administered with the moderate or strong CYP3A4 inducer relative to administration of atogepant alone. In embodiments, atogepant is administered orally with or without food. In embodiments, the CYP3A4 inducer may be administered before, concomitantly with, or after atogepant is administered.

In embodiments, the present disclosure provides a method for the preventive treatment of migraine (such as the preventive treatment of episodic migraine) in a patient undergoing concurrent treatment with a weak CYP3A4 inducer, the method comprising administering 10 mg or 30 mg or 60 mg atogepant. In embodiments, atogepant is administered orally with or without food. In embodiments, the CYP3A4 inducer may be administered before, concomitantly with, or after atogepant is administered.

For example, in embodiments, the present disclosure provides a method for the preventive treatment of migraine (such as the preventive treatment of episodic migraine) in a patient undergoing concurrent treatment with topiramate, a mild CYP3A4 inducer. Topiramate is a commonly prescribed oral antiepileptic approved by the FDA and the European Medicines Agency (EMA) for the preventive treatment of migraine (100 mg/day administered in 2 divided doses) in individuals of at least 12 years of age. Topiramate blocks voltage-dependent sodium channels, inhibits carbonic anhydrase, blocks α-amino-3-hydroxy-5-methylisoxazole-4-propionic acid, and enhances gamma-aminobutyric acid-mediated inhibition. Topiramate is a mild inducer of CYP3A4 activity with a long elimination half-life of approximately 21 hours, whereas atogepant is extensively metabolized predominantly by CYP3A4 with a minor contribution from CYP2D6, and has an elimination half-life of approximately 11 hours.

In embodiments, the present disclosure provides a method for the treatment of migraine, in particular the preventive treatment of migraine (such as the preventive treatment of episodic migraine), the method comprising administering topiramate and atogepant. In embodiments, atogepant is administered with or without food. In embodiments, topiramate is administered before, concomitantly with, or after administration of atogepant. In embodiments, atogepant is administered at a dose of 10 mg or 30 mg or 60 mg once daily. In embodiments, topiramate is administered at a dose from about 1 to about 300 mg, such as from about 25 mg to about 200 mg. In embodiments, topiramate is administered at a dose of about 25 mg, or about 50 mg, or about 100 mg, or about 200 mg. In embodiments, topiramate is administered at a dose of about 100 mg/day. In embodiments, topiramate is administered in two divided doses. In embodiments, topiramate is administered at a dose of 25 mg twice daily (e.g., morning and evening), or 25 mg in the morning and 50 mg in the evening, or 50 mg in the morning and 25 mg in the evening, or 50 mg twice daily (e.g., morning and evening). In embodiments, coadministration of topiramate and atogepant reduces atogepant $AUC_{0\text{-}tau,ss}$ by about 25% and reduces atogepant $C_{max,ss}$ by about 24%.

Coadministration of Atogepant and an OATP Inhibitor

Co-administration of atogepant with single dose rifampin, an OATP inhibitor, increased atogepant AUC by 2.85-fold and Cmax by 2.23-fold in healthy subjects.

In embodiments, the present disclosure provides a method for the preventive treatment of migraine (such as the preventive treatment of episodic migraine) in a patient undergoing concurrent treatment with an OATP inhibitor, the method comprising administering 10 mg or 30 mg atogepant once daily. In embodiments, coadministration of 10 mg or 30 mg atogepant with an OATP inhibitor results in an increase in atogepant AUC of about 2.8-fold or less relative to administration of atogepant alone. In embodiments, coadministration of 10 mg or 30 mg atogepant with an OATP inhibitor results in an increase in atogepant Cmax of about 2.2-fold or less relative to administration of atogepant alone. In embodiments, atogepant is administered orally with or without food. In embodiments, the OATP inhibitor may be administered before, concomitantly with, or after atogepant is administered.

Coadministration of Atogepant and Rifampin

As discussed above, atogepant is metabolized by CYP3A4 with a minor contribution from CYP2D6, and is also a substrate of several membrane transporters, including P-gp and OATP1B1. Rifampin is an inducer of both CYP3A4 and P-gp, while also being an inhibitor of OATP in-vitro.

The present inventors have determined that, when a single dose of atogepant 60 mg is coadministered with a single dose of rifampin 600 mg, atogepant $AUC_{0-24}$ and $C_{max}$ were 2.85-fold and 2.23-fold higher, respectively, than administration of atogepant alone. These increases in atogepant $C_{max}$ and AUC could be clinically significant. Without being bound to any particular theory, the increase in atogepant $C_{max}$ and $AUC_{0-24}$ after co-administration of single-dose rifampin represents the inhibition of the influx transporter OATP in the liver by rifampin, resulting in a reduced availability of atogepant to the hepatocytes for metabolism, thus leading to higher atogepant levels in plasma.

The present inventors have further determined that, when a single dose of atogepant 60 mg is coadministered with multiple-dose of rifampin 600 mg, atogepant $AUC_{0-inf}$ and $AUC_{0-t}$ were reduced by 61% and 60%, respectively, and $C_{max}$ was reduced by 30%, relative to administration of atogepant alone. Without being bound to any particular theory, the decrease in atogepant $C_{max}$ and AUC after coadministration with multiple-dose rifampin represents the induction of P-gp and CYP3A4, resulting in a decreased rate of absorption and increased rate of metabolism of atogepant, respectively. Systemic clearance was increased from 22.8 L/h following atogepant administration alone to 58.3 L/h following atogepant administration in the presence of multiple-dose rifampin. Without being bound to any particular theory, the reduction in $T_{1/2}$ represents the induction of CYP3A4 by rifampin, leading to an increased elimination rate of plasma atogepant and an increase in the slope of the terminal elimination phase. Although rifampin is likely still inhibiting OATP after five days of rifampin dosing, overall the inductive effects on CYP3A4 and P-gp outweigh the inhibition of OATP, resulting in a decrease of atogepant exposure with multiple-dose rifampin.

The present disclosure provides a method of preventing migraine in a patient, the method comprising administering 10 mg, 30 mg, or 60 mg atogepant once daily, wherein if the patient is coadministered multiple doses of rifampin, the patient is administered 30 mg or 60 mg atogepant once daily. In embodiments, 30 mg or 60 mg atogepant once daily is administered when the patient is administered multiple doses of rifampin, despite an increase in atogepant $AUC_{0-24}$ and $C_{max}$ of 2.85-fold and 2.23-fold, respectively, if atogepant is administered with a single dose of rifampin. In embodiments, coadministration of 30 mg or 60 mg atogepant once daily with multiple doses of rifampin results in a decrease in atogepant AUC of about 60% or less relative to administration of atogepant alone. In embodiments, coadministration of 30 mg or 60 mg atogepant once daily with multiple doses of rifampin results in a decrease in atogepant Cmax of about 30% relative to administration of atogepant alone. In embodiments, atogepant is administered orally with or without food. In embodiments, rifampin may be administered before, concomitantly with, or after atogepant is administered.

In embodiments, the present disclosure provides a method of preventing migraine in a patient undergoing concurrent treatment with a drug that is a strong inducer of CYP3A4 and an inhibitor of OATP, the method comprising administering 30 mg or 60 mg atogepant once daily. In embodiments, coadministration of 30 mg or 60 mg atogepant once daily with multiple doses of the CYP3A4 inducer/OATP inhibitor results in a decrease in atogepant AUC of about 60% or less relative to administration of atogepant alone. In embodiments, coadministration of 30 mg or 60 mg atogepant once daily with multiple doses of the CYP3A4 inducer/OATP inhibitor results in a decrease in atogepant Cmax of about 30% or less relative to administration of atogepant alone. In embodiments, atogepant is administered orally with or without food.

Methods for the Preventive Treatment of Migraine in Patients with Renal Impairment The renal route of elimination plays a minor role in the clearance of atogepant. Using a population pharmacokinetic analysis based on estimated creatinine clearance (CLcr), the present inventors determined that there is no significant difference in the pharmacokinetics of atogepant in patients with mild or moderate renal impairment (CLcr 30-89 mL/min) relative to those with normal renal function (CLcr>90 mL/min).

In embodiments, the present disclosure provides a method for the preventive treatment of migraine in patients having mild renal impairment (glomelular filtration rate [GFR] 60-90 mL/min), the method comprising administering 10 mg or 30 mg or 60 mg atogepant once daily. In embodiments, atogepant is taken orally with or without food. In embodiments, administration of 10 mg or 30 mg or 60 mg atogepant once daily to a patient having mild renal impairment results in an increase in atogepant $C_{max}$ of less than about 20%, such as less than about 15%, or less than about 13%, relative to patients with normal renal function. In embodiments, administration of 10 mg or 30 mg or 60 mg atogepant once daily to a patient having mild renal impairments results in an increase in atogepant 24-hour AUC of less than about 30%, such as less than about 25%, or less than about 20%.

In embodiments, the present disclosure provides a method for the preventive treatment of migraine in patients having moderate renal impairment (GFR 30-60 mL/min), the method comprising administering 10 mg or 30 mg or 60 mg atogepant once daily. In embodiments, atogepant is taken orally with or without food. In embodiments, administration of 10 mg or 30 mg or 60 mg atogepant once daily to a patient having moderate renal impairment results in an increase of atogepant $C_{max}$ by less than about 20%, such as less than about 15%, or less than about 13%, relative to patients with normal renal function. In embodiments, administration of 10 mg or 30 mg or 60 mg atogepant results in an increase in atogepant 24-hour AUC of less than about 50%, or less than about 45%, relative to patients with normal renal function.

In embodiments, atogepant dose adjustment may be required in patients with severe renal impairment (CLcr 15-29 mL/min) or end stage renal disease (CLcr<30 mL/min). In embodiments, the present disclosure provides a method for the preventive treatment of migraine in patients having severe renal impairment, the method comprising administering 10 mg atogepant once daily to a patient having severe renal impairment (CLcr 15-29 mL/min). In embodiments, the present disclosure provides a method for the preventive treatment of migraine in patients having end stage renal disease (CLcr<30 mL/min), the method comprising administering 10 mg atogepant once daily to a patient having end stage renal disease. In embodiments, atogepant is taken orally with or without food.

Methods for the Preventive Treatment of Migraine in Patients Having Hepatic Impairment In embodiments, the present disclosure provides methods of safely administering atogepant to patients having mild or moderate hepatic impairment for the preventive treatment of migraine, such as episodic migraine. In embodiments, the hepatic impairment is pre-existing.

The term "hepatic impairment" refers to scoring based on the Child-Pugh Score of A, B, and C. In embodiments, mild hepatic impairment refers to Child-Pugh Class A; moderate hepatic impairment refers to Child-Pugh Class B; and severe hepatic impairment refers to Child-Pugh Class C.

In patients with pre-existing mild (Child-Pugh Class A), moderate (Child-Pugh Class B), or severe hepatic impairment (Child-Pugh Class C), it was determined that the total atogepant exposure was increased by 24%, 15%, and 38%, respectively.

In embodiments, the present disclosure provides methods for the preventive treatment of migraine in patients having mild or moderate hepatic impairment, the method comprising administering atogepant 10 mg or 30 mg or 60 mg once daily. In embodiments, atogepant is administered with or without food.

In embodiments, the present disclosure provides methods for the preventive treatment of migraine in patients having hepatic impairment, the method comprising administering 10 mg or 30 mg or 60 mg once daily, wherein if the patient develops severe hepatic impairment (Child-Pugh Class C), atogepant treatment is discontinued.

Transaminase Elevations in Atogepant-Treated Patients vs. Placebo

In embodiments, the present disclosure provides methods for the preventive treatment of migraine, such as the preventive treatment of episodic migraine, comprising administering atogepant, wherein the treatment with atogepant does not significantly affect the level of liver enzymes, such as alanine aminotransferase (ALT) or aspartate aminotransferase (AST).

In embodiments, the present disclosure provides a method for the preventive treatment of migraine in a population of patients, the method comprising administering 10 mg or 30 mg or 60 mg atogepant once daily to the population of patients, wherein the rate of transaminase elevations over 3 times the upper limit of normal (ULN) in the population of patients is lower than a rate of transaminase elevations over 3 times the upper limit of normal in a population of patients treated with placebo. In embodiments, atogepant is administered to the population of patients for at least 3 weeks, or at least about 6 weeks, or at least about 9 weeks, or at least about 12 weeks, or at least about 16 weeks, or at least about 20 weeks, or at least about 24 weeks, or at least about 52 weeks, and the rate of transaminase elevations over 3 times the upper limit of normal (ULN) in the population of patients is lower than a rate of transaminase elevations over 3 times the upper limit of normal in a population of patients treated with placebo.

Food Effect

As previously mentioned, the present disclosure provides methods for the preventive treatment of migraine, such as the preventive treatment of episodic migraine, by administering 10 mg or 30 mg or 60 mg atogepant once daily to a patient in need thereof. In embodiments, atogepant may be taken without regard to whether a patient has eaten, sometimes referred to as "without regard to meals", "can be taken with or without food", "no food effect", or similar phrases.

More particularly, the inventors of the present disclosure have determined that, while a statistically significant food effect is demonstrated on the pharmacokinetics of atogepant, this food effect is not clinically relevant, and a patient can take atogepant with or without food. Accordingly, atogepant can advantageously be taken at any time regardless of whether the patient has recently eaten.

Generally, a fasted state refers to the fact that a patient has not eaten for a given amount of time before taking a dose of medication, as well as not eating for a given amount of time after taking the dosage form. These time periods before and after dosing can range between, for example, 2 hours to 24 hours. A fed state generally refers to the fact that a patient has eaten within a given time period of taking a particular medication. The time period is variable but may constitute, for example, a meal just before, during, or just after taking the medication, such as within about an hour of dosing. The quantity of food eaten that will qualify as a fed state is also variable but generally can comprise between about 500 to about 1500 kcal of food.

Example 1

A single-center, Phase 1, open-label, two treatment, two period, single sequence, non-randomized crossover interaction study between atogepant and rifampin in 32 healthy, adult male or female participants between the ages of 18 and 45 years of age, inclusive, was conducted.

The study consisted of a Screening Visit, two study periods, an end-of-treatment (EOT) visit, and a follow-up visit. During Study Periods 1 and 2. participants received a total of three treatments with two atogepant washout periods, as described in Table 1.

TABLE 1

| Study Design | |
|---|---|
| Screening (Days −14 to −1) | Was to be conducted within 14 days before Day 1 |
| Period 1 (Days −1 to 5) | Participants were to stay at the study center overnight on Days −1, 1, and 2 and discharged from the study center on Day 3. In this period, participants received:<br>Treatment A: A single 60 mg atogepant dose on Day 1<br>No procedures were performed on Days 4 and 5 and participants were not required to return to the study center. Days 4 and 5 were a continuation of the first 6-day washout period for atogepant following the first single dose on Day 1. |
| Period 2 (Days 6 to 14) | Participants were to stay at the study center overnight on Days 6 and 7 and were discharged from the study center on Day 8. Participants returned for outpatient visits on Days 9 and 10. On Day 11, participants returned to the study center to stay overnight on Days 11, 12, and 13, and were discharged from the study center on Day 14. In this period, participants received:<br>Treatment B1: Co-administration of 60 mg atogepant and 600 mg rifampin on Day 7 followed by 600 mg rifampin alone, once daily, on Days 8, 9, 10, and 11. Participants received rifampin on an outpatient basis on Days 9 and 10.<br>Treatment B2: Co-administration of 60 mg atogepant and 600 mg rifampin on Day 12 followed by 600 mg rifampin alone on Day 13.<br>The second atogepant washout period was 5 days between Treatment B1 and B2 (from Day 7 to Day 12). |
| EOT Visit | Was conducted on Day 14, within 7 days after Day 14 on an outpatient basis, or at the time of early termination. |
| Follow-Up Visit | Was conducted on an outpatient basis on Day 43 (±2 days) or 30 (±2 days) days after the last dose of study treatment if a participant discontinued dosing early. |

Study assessments included blood sample collections for evaluation of atogepant plasma PK and plasma trough concentrations of rifampin. In addition, the safety and tolerability of atogepant when given alone and in combination with rifampin was monitored throughout the study by clinical assessment of AEs and by measurement of vital signs, physical examinations, 12-lead ECGs, and clinical laboratory tests (hematology, serum chemistry, and urinalysis).

Not including screening, the anticipated duration of study participation was a maximum of 46 days (Day −1 through the follow-up visit on Day 43 (±2 days)).

Inclusion criteria included healthy male or female participants, 18 to 45 years of age with a BMI≥18 kg/$m^2$ and ≤30 kg/$m^2$. Participants were non-smokers and non-users of nicotine-containing products and had negative urine drug screens.

Participants who had a clinically significant disease state, in the opinion of the examining investigator or designee, in any body system or who had any clinical condition or previous surgery that could have affected the absorption, distribution, biotransformation, or excretion of atogepant or rifampin were excluded from the study. Participants also could not have had a history of alcohol or other substance abuse within the previous 5 years.

The study treatments that were administered (atogepant and rifampin) and the dosing regimens (Treatment A, Treatment B1, and Treatment B2) are described below:

- Treatment A: A single dose of 60 mg atogepant (1×60 mg tablet) on Day 1
- Treatment B1: Co-administration of 60 mg atogepant and 600 mg rifampin (2×300 mg capsules) on Day 7 and 600 mg rifampin alone, once daily, on Days 8, 9, 10, and 11
- Treatment B2: Co-administration of 60 mg atogepant and 600 mg rifampin on Day 12 and 600 mg rifampin alone on Day 13.

The atogepant washout period was 6 days between Treatments A and B1 and 5 days between Treatments B1 and B2.

There were three analysis populations used for analysis of data from this study:

- The Safety Population consisted of all participants who received at least one dose of study treatment.
- The PK Population for atogepant consisted of all participants who had evaluable PK parameters for atogepant following all treatments (Treatments A, B1, and B2).
- The PK Population for rifampin consisted of all participants who had measurable plasma concentrations for rifampin.

The mean age of participants in the safety population was 31.3 years. The proportion of female participants was higher than that for male participants (59.4% versus 40.6%). White and black or African American participants accounted for 50.0% and 46.9% of the safety population, respectively; 1 (3.1%) was Asian. Nineteen (59.4%) participants were non-Hispanic and 13 (40.6%) were of Hispanic ethnicity. The mean BMI of the safety population was 25.67 kg/$m^2$.

When atogepant was to be administered alone or in combination with rifampin, participants were required to undergo a 10-hour overnight fast prior to dosing (beginning on Days −1, 6, and 11) and were required to maintain the fast for an additional 4 hours following dose administration (on Days 1, 7, and 12).

When rifampin was to be administered alone (on Days 8, 9, 10, 11, and 13), no food should have been administered for 1 hour before and 1 hour after dosing.

All treatments were administered with approximately 240 mL of water; water was provided for participants at other times as desired, except for 1 hour before and after dose administration.

Relative to the time that atogepant was administered, blood samples for atogepant plasma PK were to be collected at the following times:

- Days 1 and 12: 0 hour (predose) and at 0.5, 1, 1.5, 2, 3, 4, 6, 8, 12, 16, 24, 36, and 48 hours post dose.
- Day 7: 0 hour (predose) and at 0.5, 1, 1.5, 2, 3, 4, 6, 8, 12, 16, and 24 hours postdose Blood samples for plasma trough concentrations of rifampin were to be collected at:

- Days 11 and 12:0 hour (predose) prior to rifampin administration

Figure 2:
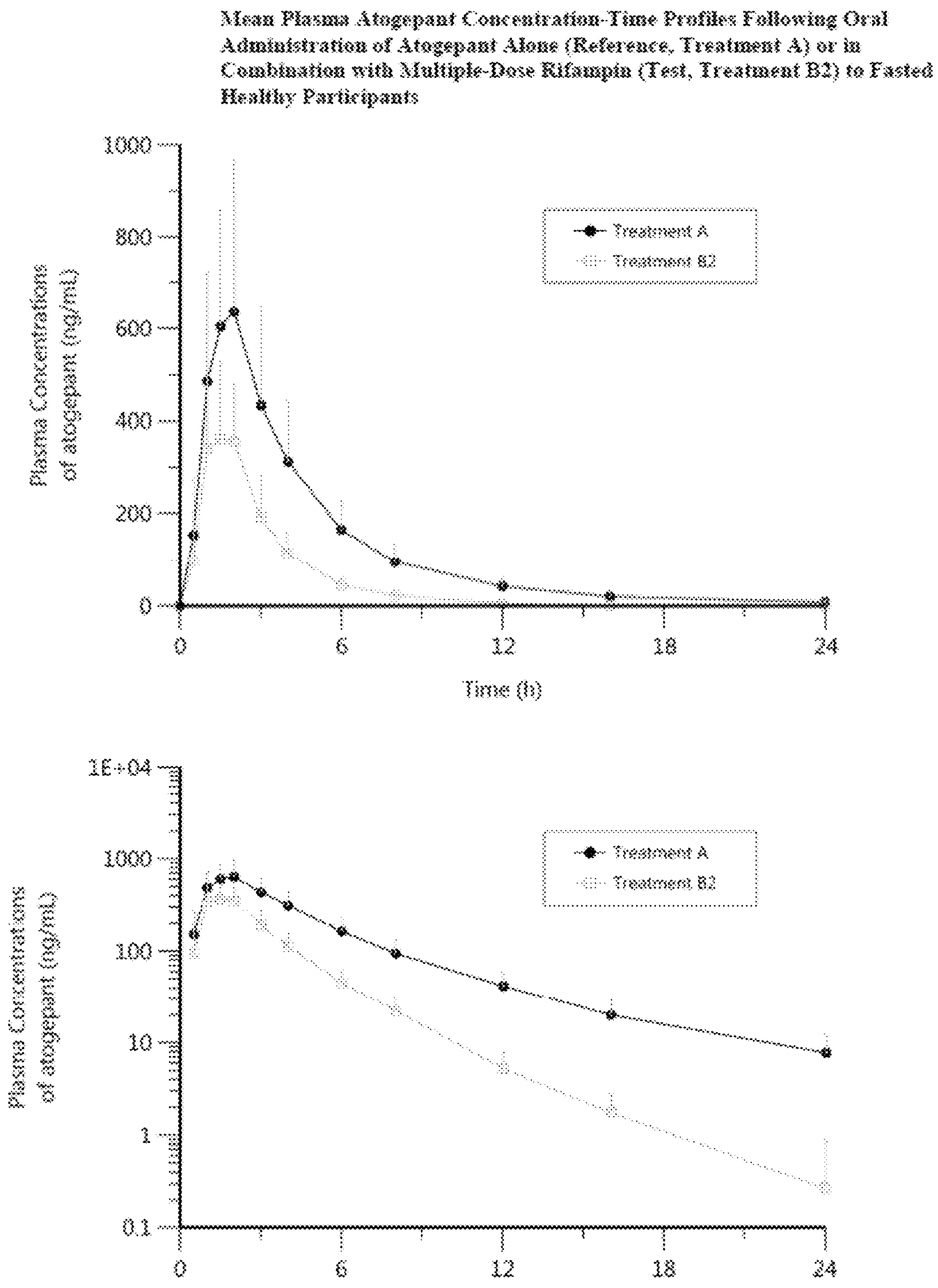
FIG. 2 shows the mean plasma atogepant concentration-time profiles following oral administration of atogepant alone or in combination with multiple-dose rifampin to Fasted Healthy Participants.

The mean plasma atogepant concentration-time profiles are presented in FIGS. 1 and 2. In particular, FIG. 1 illustrates the mean plasma atogepant concentration-time profiles following administration of atogepant alone (Reference, Treatment A) or in combination with single-dose rifampin (Test, Treatment B1) to Fasted Healthy Participants. FIG. 2 provides the mean plasma atogepant concentration-time profiles following oral administration of atogepant alone (Reference, Treatment A) or in combination with multiple-dose rifampin (Test, Treatment B2) to Fasted Healthy Participants.

A summary of the mean PK parameters for atogepant when administered alone or in combination with rifampin is presented in Table 2.

TABLE 2

Mean (SD) Atogepant Pharmacokinetic Parameters following Atogepant 60 mg Alone on Day 1 (Treatment A), or in Combination with 600 mg Rifampin on Day 7 Followed by 600 mg Rifampin Alone, Once Daily, on Days 8, 9, 10, and 11 (Treatment B1) or in Combination with 600 mg Rifampin on Day 12 Followed by 600 mg Rifampin Alone on Day 13 (Treatment B2) (PK Population)

| PK Parameter | Treatment A N = 31 | Treatment B1 N = 31 | Treatment B2 N = 31 |
|---|---|---|---|
| $T_{max}$ (h)[a] | 1.50 (0.500-2.00) | 2.00 (1.00-4.00) | 1.50 (1.00-3.00) |
| $C_{max}$ (ng/mL) | 711 (328) | 1550 (624) | 487 (192) |
| $AUC_{0-24}$ (ng · h/mL) | 2870 (1060) | 8130 (3260) | — |
| $AUC_{0-t}$ (ng · h/mL) | 2960 (1100) | — | 1180 (358) |
| $AUC_{0-\infty}$ (ng · h/mL) | 3000 (1100) | — | 1130[b] (332) |
| $t_{1/2}$ (h) | 11.4 (5.55) | — | 2.39[b] (1.09) |
| $V_z/F$ (L) | 390 (271) | — | 197[b] (105) |
| CL/F (L/h) | 22.8 (8.44) | — | 58.3[b] (21.8) |
| λz (1/h) | 0.0778 (0.411) | — | 0.325[b] (0.0833) |

TABLE 2-continued

| Mean (SD) Atogepant Pharmacokinetic Parameters following Atogepant 60 mg Alone on Day 1 (Treatment A), or in Combination with 600 mg Rifampin on Day 7 Followed by 600 mg Rifampin Alone, Once Daily, on Days 8, 9, 10, and 11 (Treatment B1) or in Combination with 600 mg Rifampin on Day 12 Followed by 600 mg Rifampin Alone on Day 13 (Treatment B2) (PK Population) | | | |
|---|---|---|---|
| PK Parameter | Treatment A N = 31 | Treatment B1 N = 31 | Treatment B2 N = 31 |

[a]Median (Range)
[b]N = 28

The median $T_{max}$ value for atogepant as similar following atogepant administered alone compared with in combination with single-dose or after multiple dose rifampin (Treatments B1 and B2, respectively). The mean apparent $T_{1/2}$ of atogepant was reduced by approximately 9 hours (11.4 hours vs. 2.39 hours) following atogepant administered alone compared with in combination with multiple dose rifampin.

Treatment B1/Treatment A: In the comparison of a single dose of atogepant 60 mg coadministered with single dose of rifampin 600 mg (Test) versus a single dose of atogepant 60 mg administered alone (Reference), Atogepant $AUC_{0-24}$ and $C_{max}$ were 2.85-fold and 2.23-fold higher, respectively. These increases in atogepant $C_{max}$ and AUC could be clinically significant.

Treatment B2/Treatment A: In the comparison of a single dose of atogepant 60 mg coadministered with multiple-dose of rifampin 600 mg (Test) versus a single dose of atogepant 60 mg atogepant administered alone (reference), atogepant $AUC_{0-\infty}$ and $AUC_{0-t}$ were reduced by 61% and 60%, respectively, and $C_{max}$ was reduced by 30%. These decreases in atogepant $C_{max}$ and AUC could be clinically significant.

TABLE 3

Summary of Statistical Analysis Results of Plasma Atogepant Pharmacokinetic Parameters Following Oral Administration of Single Dose 600 mg Rifampin in Combination with 60 mg Atogepant (Treatment B1, Test) in Comparison to 60 mg Atogepant Administered Alone (Treatment A, Reference) in Healthy Adult Participants (N = 31, PK population)

| PK | Geometric LSM | | Ratio of Geometric Means (%) | 90% Lower Confidence | 90% Upper Confidence |
|---|---|---|---|---|---|
| Parameter | Test | Reference | Test/Ref | Interval | Interval |
| $AUC_{0-24}$ (ng · h/mL) | 7631.86 | 2679.39 | 284.84 | 260.29 | 311.69 |
| $C_{max}$ (ng/mL) | 1444.14 | 648.61 | 222.65 | 198.55 | 249.68 |

TABLE 4

Summary of Statistical Analysis Results of Plasma Atogepant Pharmacokinetic Parameters Following Oral Administration of Multi-Dose 600 mg Rifampin in Combination with 60 mg Atogepant (Treatment B2, Test) in Comparison to 60 mg Atogepant Administered Alone (Treatment A, Reference), in Healthy Adult Participants (N = 31, PK Population)

| PK | Geometric LSM | | Ratio of Geometric Means (%) | 90% Lower Confidence | 90% Upper Confidence |
|---|---|---|---|---|---|
| Parameter | Test | Reference | Test/Ref | Interval | Interval |
| $AUC_{0-\infty}$ (ng · h/mL) | 1091.54 | 2809.41 | 38.85 | 34.56 | 43.68 |
| $AUC_{0-t}$ (ng · h/mL) | 1121.66 | 2772.16 | 40.46 | 36.16 | 45.28 |
| $C_{max}$ (ng/mL) | 454.44 | 648.61 | 70.06 | 60.27 | 81.44 |

A statistically significant increase in atogepant systemic exposure (2.85-fold for $AUC_{0-24}$ and 2.23-fold for $C_{max}$) was observed following coadministration of single-dose atogepant 60 mg and single-dose rifampin 600 mg compared with administration of single-dose atogepant 60 mg alone. Rifampin is an OATP1B1 inhibitor and atogepant metabolism is dependent on the influx of atogepant in the hepatocyte through the OATP1B1 transporter. The increases in atogepant $C_{max}$ and AUC when coadministered with OATP1B1 inhibitors could be clinically significant and atogepant dose adjustment may be required.

A statistically significant decrease in atogepant systemic exposure (61% for $AUC_{0-\infty}$, 60% for $AUC_{0-t}$, and 30% for $C_{max}$) was observed following coadministration of single dose atogepant 60 mg and multiple-dose rifampin 600 mg compared with administration of single-dose atogepant 60 mg alone. Rifampin is a strong CYP3A4 inducer and a P-gp inducer, and atogepant is extensively metabolized by CYP3A4 and is also a substrate of P-gp. The decreases in atogepant $C_{max}$ and AUC when coadministered with strong CYP3A4 and P-gp inducers could be clinically significant and atogepant dose adjustment may be required.

Safety analyses were based on the safety population (i.e., all patients who received ≥1 dose of study treatment). Safety measurements included TEAE recordings, clinical laboratory determinations, vital sign parameters, ECG results, and physical examination findings.

All 32 participants received a single 60 mg dose of atogepant on Day 1 (Treatment A); 31 participants received co-administration of 60 mg atogepant and 600 mg rifampin on Day 7 followed by 600 mg rifampin alone, once daily, on days 8 to 11 (Treatment B1) and co-administration of 60 mg atogepant and 600 mg rifampin on day 12 followed by 600 mg rifampin alone on day 13 (Treatment B2). Mean duration of treatment for all participants was 12.6 days.

Overall, atogepant and rifampin were well tolerated during the study. Table 5 provides a summary of AEs by treatment for the safety population. No deaths or SAEs occurred during the study; no participants had TEAEs that led to discontinuation. A total of 11 (34.4%) participants had TEAEs during the study, 8 (25.8%) after administration of Treatment B1 and 5 (16.1%) after administration of treatment B2. No participants reported a TEAE after receiving Treatment A.

TABLE 5

Overall Summary of Adverse Events

| | Treatment A (N = 32) n (%) | Treatment B1 (N = 31) n (%) | Treatment B2 (N = 31) n (%) | All participants (N = 32) n (%) |
|---|---|---|---|---|
| Treatment-emergent adverse events (TEAE) | 0 | 8 (25.8) | 5 (16.1) | 11 (34.4) |
| Deaths | 0 | 0 | 0 | 0 |
| Treatment-Emergent Serious Adverse Events (TESAE) | 0 | 0 | 0 | 0 |
| TEAE leading to treatment discontinuation | 0 | 0 | 0 | 0 |

The most common TEAE (those occurring in at least 2 participants with a specific treatment) reported after administration of B1 was headache, which occurred in 2 (6.5%) of participants. All TEAEs that were reported after administration of Treatment B2 occurred in 1 (3.2%) participant each.

A total of 5 (15.6% participants had at least one treatment-related TEAE during the study; 4 (12.9%) after administration of Treatment B1 and 2 (6.5%) after administration of Treatment B2. The most common treatment related TEAE was nausea (2 [6.3%] participants, one after Treatment B1 and one after Treatment B2). All other treatment-related TEAEs occurred in 1 participant each and included abdominal discomfort, diarrhea, vomiting, abdominal pain, arthralgia, dizziness, headache, and chromaturia.

All TEAEs were mild (10 [31.3%] participants) or moderate (1 [3.1%] participant); no severe TEAEs were reported. Moderate TEAEs included nausea and vomiting reported by 1 participant after administration of Treatment B1.

There were no notable changes from baseline in clinical laboratory test results, vital signs, parameters, and ECG findings. There were no participants whose laboratory values met Hy's Law criteria.

Study treatments, single-dose atogepant alone or single-dose atogepant co-administered with single- or multiple-dose rifampin

Example 2

An open-label, single-sequence drug-drug interaction study was carried out to evaluate the effect of CYP3A4 inhibition by oral itraconazole (200 mg per day) on the pharmacokinetics of a single oral dose of atogepant (60 mg) in healthy subjects.

The primary objective of this study was to assess the effects of multiple dose itraconazole on the pharmacokinetics of a single dose of atogepant. The primary endpoints were PK parameters of atogepant derived from plasma concentrations. The secondary objectives of the study were to assess the safety and tolerability of atogepant and itraconazole given alone and in combination, and to establish the correlation between concentrations of atogepant in dried blood sample (DBS) (obtained via finger stick) and plasma. The secondary endpoints included AEs, clinical laboratory parameters, vital signs, ECG, and physical examination, and correlation of concentrations of atogepant in DBS and plasma.

This study was a single-center, single-sequence, open-label, 2-period PK drug-interaction study in 40 healthy male and female subjects aged 18 through 45 years.

For enrollment into the study, each subject had to meet all of the following inclusion criteria and none of the following exclusion criteria.

Inclusion Criteria

- Be a healthy male or female, aged 18 through 45 years, inclusive
- If female, had a negative result from a serum pregnancy test at screening and a negative result from a serum or urine pregnancy test on day −1
- If male, agreed to use an effective method of contraception and not have their partners become pregnant throughout the study, or had been sterilized for at least one year
- If female of childbearing potential, agreed to use an effective method of contraception and not become pregnant throughout the study.
- Be nonsmoking (never smoked or had not smoked within the previous 2 years)
- Had a body mass index (BMI) ≥18 kg/m$^2$ and ≤30 kg/m$^2$.
- Had a sitting pulse rate ≥60 bpm and ≤100 bpm during the vital signs assessment at screening.

Exclusion Criteria

- Known hypersensitivity to atogepant or other CGRP receptor antagonist or itraconazole
- Clinically significant disease state, in the opinion of the examining physician, in any body system.
- Sitting systolic blood pressure (SBP)≥140 mm Hg or ≤90 mm Hg or sitting diastolic blood pressure (DBP)≥90 mm Hg or ≤60 mm Hg at screening
- Abnormal ECG results thought to be potentially clinically significant (PCS) or QT prolongation (QTcF≥450 msec or uncorrected QT≥500 msec) according to the investigator
- Positive test results for anti-human immunodeficiency virus type 1 or 2, hepatitis B surface antigen, or anti-hepatitis C virus at screening
- Abnormal and clinically significant results on physical examination, medical history, serum chemistry, hematology, coagulation, or urinalysis
- History of alcohol or other substance abuse within the previous 5 years
- Positive test results for benzoylecgonine (cocaine), methadone, barbiturates, amphetamines, benzodiazepines, alcohol, cannabinoids, opiates, phencyclidine, or cotinine at screening or Day −1.
- Participation in any other clinical investigation using an experimental drug requiring repeated blood or plasma draws within 60 days of IP administration.
- Participation in a blood or plasma donation program within 60 or 30 days, respectively, of IP administration
- Consumption of caffeine within 48 hours, grapefruit-containing products or vegetables from the mustard greens family (e.g., kale, broccoli, watercress, collard greens, kohlrabi, Brussels sprouts, mustard) within 14 days, or consumption of alcohol within 72 hours before administration of IP.
- Any clinical condition or previous surgery that might have affected the absorption, distribution, biotransformation, or excretion of atogepant or itraconazole
- Taken any concomitant medications (including over the counter medications) within 14 days or hormonal drug products within 30 days before administration of IP
- Previously taken atogepant or previously participated in an investigational study of atogepant or MK-8031.
- Breastfeeding.

Subjects who satisfied the inclusion and exclusion criteria were assigned to a single fixed-treatment sequence in which they received Treatment A followed by Treatment B; there was a 7-day washout period between treatments.

- Treatment A: Single oral 60 mg dose of atogepant (tablet) under fasted conditions on Day 1
- Treatment B
  - Days 8-14: Itraconazole 200 mg (tablet) orally once daily under fed conditions.
  - Day 15: Itraconazole 200 mg coadministered with atogepant 60 mg (tablet) under fasted conditions.
  - Days 16 to 17: Itraconazole 200 mg (tablet) once daily under fed conditions.

Atogepant was administered in the fasted state in this study. Administration of itraconazole with food enhances its bioavailability. Accordingly, to maximize the CYP3A4 inhibition effect, itraconazole was administered with food on all the itraconazole treatment days except day 15. On day 15, both itraconazole and atogepant were administered under fasted state. Fasted state administration of itraconazole on Day 15 was unlikely to affect the CYP3A4 inhibition effect due to the attainment of steady state (of CYP3A4 activity) and long $T_{1/2}$ of itraconazole (34 to 42 hours) following repeat dose administration.

The total duration of study participation for each subject was approximately 48 days excluding the screening visit (Day −1 through Day 47). The study included 8 overnight stays.

The mean age of participants was 34.8 years with a range from 19 to 45 years. Eighteen (45%) subjects were male and 22 (55%) were female. A total of 33 (82.5% subjects were white and 7 (17.5%) were black or African American. Overall, 37 (92.5%) were Hispanic or Latino and 3 (7.5%) were not Hispanic or Latino. Mean (SD) BMI was 27.41 (2.47) kg/m$^2$.

Figure 3:
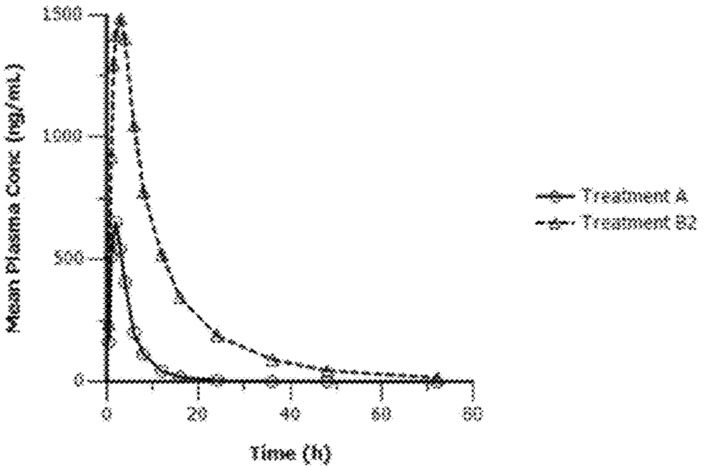
FIG. 3 shows the mean plasma concentrations of atogepant after the administration of 60 mg either alone or in the presence of steady state itraconazole, a strong CYP3A4 inhibitor.
Figure 4:
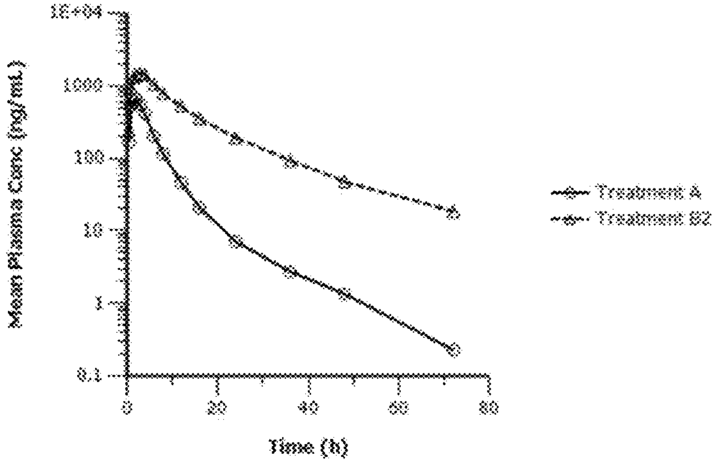
FIG. 4 shows a semilogarithmic plot of the mean plasma concentrations of atogepant 60 mg either alone or in the presence of steady state itraconazole.

Mean plasma concentrations of atogepant after the administration of 60 mg either alone or in the presence of steady state itraconazole are presented in FIG. 3. A semilogarithmic plot of the mean plasma concentrations of atogepant is presented in FIG. 4. Mean (SD) PK parameters and the results of statistical analysis are provided in Table 6.

TABLE 6

PK Parameters of Atogepant Following Treatment A (60 mg single-dose Atogepant) and Treatment B (60 mg single-dose Atogepant + Itraconazole) in Healthy Subjects

| PK Parameter | Atogepant Alone (Treatment A; N = 40) | Atogepant + Itraconazole (Treatment B; N = 40) | GM Ratio (%) Treatment B/ Treatment A | 90% CI |
|---|---|---|---|---|
| $C_{max}$ (ng/mL) | 740 (231) | 1580 (469) | 215.11 | 195.25, 236.99 |
| $AUC_{0-t}$ (ng · h/mL) | 3440 (1030) | 18500 (4860) | 543.26 | 501.54, 588.45 |
| $AUC_{0-\infty}$ (ng · h/mL) | 3470 (1040) | 18900 (4990) | 550.78 | 508.64, 596.42 |
| $T_{max}$ (h) | 2.0 (1.0-3.0)* | 3.0 (1.5-4.0)* | 1.0** | — |
| $\lambda_z$ (1/h) | 0.0825 (0.0412) | 0.0496 (0.0122) | — | — |

TABLE 6-continued

PK Parameters of Atogepant Following Treatment A (60 mg single-dose Atogepant) and Treatment B (60 mg single-dose Atogepant + Itraconazole) in Healthy Subjects

| PK Parameter | Atogepant Alone (Treatment A; N = 40) | Atogepant + Itraconazole (Treatment B; N = 40) | GM Ratio (%) Treatment B/ Treatment A | 90% CI |
|---|---|---|---|---|
| $T_{1/2}$ (h) | 11.2 (7.78) | 14.9 (3.96) | — | — |
| CL/F (L/h) | 19.2 (7.49) | 3.46 (1.18) | — | — |
| Vz/F (L) | 292 (175) | 73.4 (34.4) | — | — |

*Median (min-max)

The $C_{max}$ and AUC of atogepant increased by 2.15-fold and 5.5-fold, respectively, due to inhibition of CYP3A4 by itraconazole. Such an increase in exposure of atogepant due to CYP3A4 inhibition could be clinically significant and atogepant dose adjustment may be needed when concomitantly administered with strong CYP3A4 inhibitors.

Systemic clearance of atogepant decreased from 19.2 L/h following its administration alone to 3.46 L/h following its administration in the presence of steady state itraconazole. Accordingly, $T_{1/2}$ of atogepant increased from 11.2 hours following its administration alone to 14.9 hours due to CYP3A4 inhibition by itraconazole.

Overall, each treatment was well-tolerated. Five TEAEs were reported (2 subjects experienced dizziness [atogepant alone], 2 subjects experienced headache [itraconazole alone], and 1 subject experienced constipation [itraconazole alone]). None of the TEAEs was reported as an SAE, and all TEAEs were mild in intensity. No TEAEs led to permanent discontinuation of study treatment. No deaths occurred during the study. There were no postbaseline laboratory findings, vital signs, or ECGs that were PCS during the study.

Overall, itraconazole at steady state had a clinically significant effect on the pharmacokinetics of atogepant. These results suggest that CYP3A4 inhibition by itraconazole or other strong CYP3A4 inhibitors will result in a clinically significant increase in the exposure of atogepant. Atogepant dose reduction may be needed when concomitantly administered with strong CYP3A4 inhibitors. Each treatment regimen was well tolerated in healthy subjects.

Example 3

A multicenter, non-randomized, open-label, parallel-group, single-dose study was carried out to evaluate the PK, safety, and tolerability profiles of atogepant in participants with impaired hepatic function and matched healthy participants with normal hepatic function after a single 60-mg oral dose of atogepant. The primary outcome measures were PK parameters of atogepant derived from plasma concentrations. Safety measures were AEs, clinical laboratory determinations, vital sign parameters, electrocardiographic results, and physical examination findings.

In this study, participants with normal hepatic function and participants with hepatic impairment (mild, moderate, or severe according to the Child-Pugh classification) received a single, oral, 60-mg tablet of atogepant on Day 1 with 240 mL of water at the study center under fasted conditions. PK blood samples were collected for up to 72 hours after dose administration. The total duration of study participation for each participant was 5 days (Day −1 to Day 4), excluding the screening visit. Participants were admitted in the clinic on Day −1 and remained in the clinic until Day 4. Participants with moderate hepatic impairment were enrolled after 4 participants with mild hepatic impairment completed the study; participants with severe hepatic impairment were enrolled after 4 participants with moderate hepatic impairment completed the study. Participants with normal hepatic function were recruited after all patients with hepatic impairment were enrolled in the study. The safety and tolerability of atogepant was established in each group before the subsequent group was enrolled.

Participants had an EOS visit on or within 7 days of the final PK sample on Day 4. Participants also had a safety follow-up visit on day 30 for safety assessments.

Planned enrollment was 32 participants: 24 with hepatic impairment (8 mild, 8 moderate, and 8 severe) and 8 with normal hepatic function. All participants were 18 to 80 years of age with BMI≥18 $kg/m^2$ and ≤42 $kg/m^2$, sitting pulse rate ≥50 bpm and ≤100 bpm, and QTcF<470 msec. Participants with hepatic impairment had to have a Child-Pugh score of ≤12 and were not to be included if sitting systolic blood pressure was ≥165 mmHg or ≤95 mmHg or sitting diastolic blood pressure was ≥100 mmHg or ≤50 mmHg at screening. Participants with normal hepatic function were not to be included if sitting systolic blood pressure was ≥140 mmHg or ≤90 mmHg or sitting diastolic blood pressure was ≥90 mmHg or ≤50 mmHg at screening.

Participants were enrolled into four groups: Group I (Mild Hepatic Impairment); Group II (Moderate Hepatic Impairment); Group III (Severe Hepatic Impairment); and Group IV (Normal Hepatic Impairment). Participants with normal hepatic function were recruited after the participants with hepatic impairment were enrolled in the study so that participants could be matched as closely as possible by age range, weight range, and gender among groups. Participants were matched specifically according to rage range, not exceeding 5 years between the means of the normal group and the 3 impaired hepatic function groups combined; weight range, which deviated <20% between the means of the normal group and the 3 impaired hepatic function groups combined; and gender, as much as possible to match the ratio of the normal group to the 3 impaired hepatic function groups combined.

A total of 32 participants were enrolled: 8 with normal hepatic function, 8 with mild hepatic impairment, 8 with moderate hepatic impairment, and 8 with severe hepatic impairment. All participants completed the study through the safety follow-up period. No participants prematurely discontinued.

The mean age of the Safety Population was 58.8 years (range: 45 to 72 years), two-thirds of the population were male, the majority of participants (87.5%) were white, and the mean BMI was 30.72 $kg/m^2$. The demographic characteristics were similar across the 4 hepatic function groups except for ethnicity: three-fourths of the participants in the moderate hepatic impairment group were non-Hispanic/non-Latino, whereas in the other hepatic function groups non-Hispanic/non-Latino participants made up one-fourth to half of the participants in each group. The observed difference in distribution of ethnicity across the groups is unlikely to impact the results of the study.

No participants in the normal hepatic function group had a medical history of any hepatobiliary disorders, compared with a positive history of hepatobiliary disorders for 6/8 participants in the mild hepatic impairment cohort, 8/8 in the moderate hepatic impairment cohort, and 8/8 in the severe hepatic impairment cohort.

Participants received a single, oral, 60 mg tablet of atogepant. Each participant received only one dose of the study intervention. Participants received the atogepant tablet with 240 mL of water at the study center under fasted conditions. Following dose administration, participants continued their fast and remained seated upright and awake for 4 hours.

From 14 days before Day 1 and until all study procedures were completed, participants were to refrain from consuming grapefruit, grapefruit juice, and vegetables from the mustard green family (e.g., kale, broccoli, watercress, collard greens, kohlrabi, Brussels sprouts, mustard). From 48 hours before administration of the study intervention and until all study procedures were completed, participants were to refrain from consuming xanthine-containing compounds (products with caffeine, which included, but were not limited to, coffee, tea, soft drinks, energy sports drinks, and chocolate). Alcoholic beverages were not to be allowed from 72 hours before dosing until completion of PK blood sampling; furthermore, the participants with alcohol-induced liver cirrhosis were to abstain from alcohol for at least one week prior to administration of the study intervention and during the entire study. Participants were not to engage in strenuous activity at any time during the study.

Sampling for atogepant plasma concentrations was done starting on Day 1 at 0 hour (predose) and at 0.5, 1, 1.5, 2, 3, 4, 6, 8, 12, 16, 24, 36, 48, and 72 hours post dose.

Figure 5A:
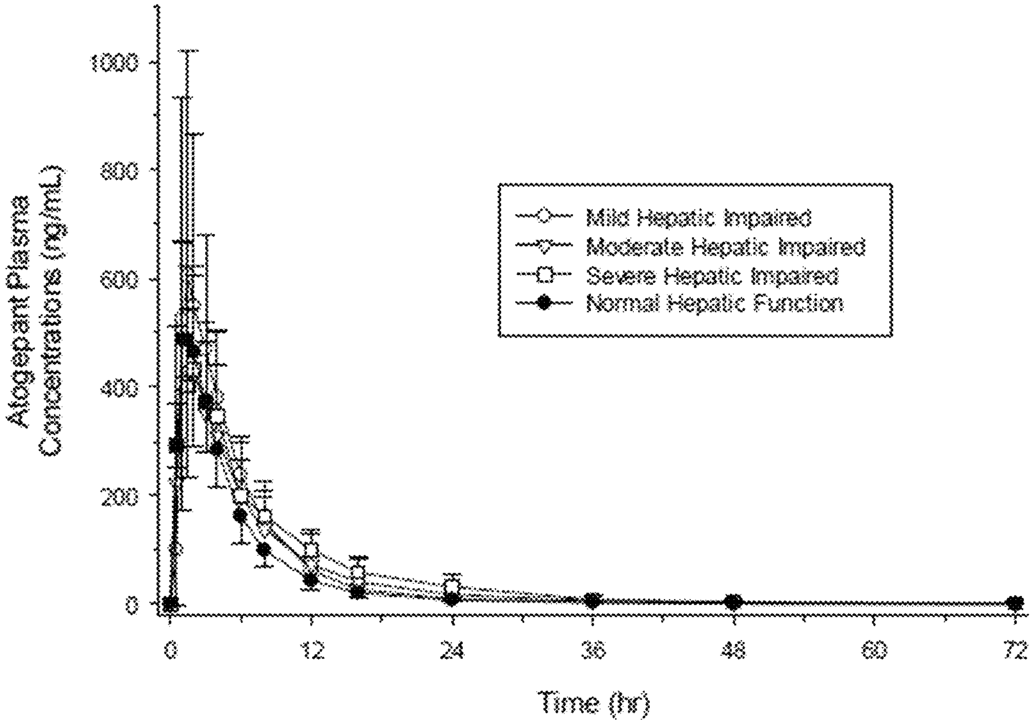
FIG. 5A shows the mean plasma atogepant concentration-time profiles (linear scale) following single dose oral administration of 60 mg atogepant in participants with mild, moderate, or severe hepatic impairment and in participants with normal hepatic function (N=8 in each group).
Figure 5B:
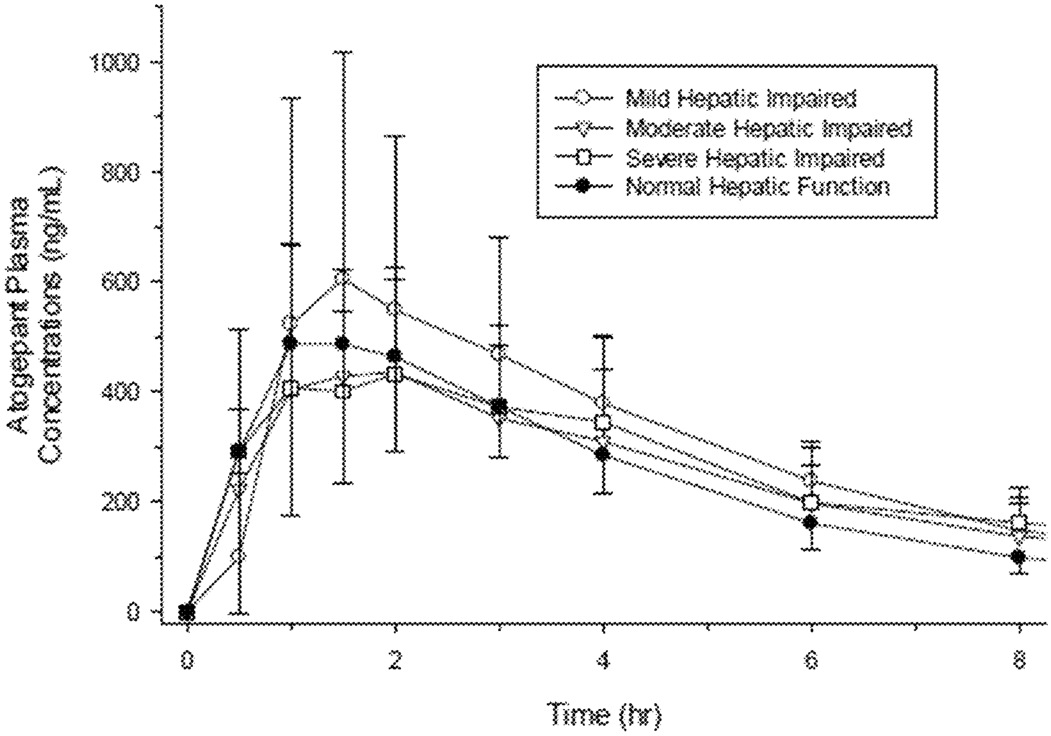
FIG. 5B shows a corresponding semi-logarithmic plot.

The mean plasma atogepant concentration-time profiles on a linear scale in participants with varying degrees of hepatic impairment and with normal hepatic function are presented in FIG. 5A. The corresponding semi-logarithmic plot is provided in FIG. 5B. A summary of the mean PK parameters for atogepant when administered to participants with varying degrees of hepatic impairment and to participants with normal hepatic function is presented in Table 7.

TABLE 7

Mean (±SD) Atogepant Pharmacokinetic Parameters Following Single Dose Oral Administration of Atogepant 60 mg in Participants with Mild, Moderate, or Severe Hepatic Impairment and in Participants with Normal Hepatic Function, PK Population

| PK Parameter | Mild Hepatic Impairment Group (N = 8) | Moderate Hepatic Impairment Group (N = 8) | Severe Hepatic Impairment Group (N = 8) | Normal Hepatic Function Group (N = 8) |
|---|---|---|---|---|
| $C_{max}$ (ng/mL) | 666.30 ± 372.13 | 528.60 ± 227.13 | 524.87 ± 197.18 | 588.65 ± 248.49 |
| $T_{max}$ (h)[a] | 1.76 (1.00-4.00) | 1.50 (1.00-6.00) | 1.00 (0.50-3.00) | 1.75 (1.00-3.00) |
| $AUC_{0-t}$ (ng · h/mL) | 3472.65 ± 1424.90 | 3270.13 ± 1693.04 | 3797.07 ± 1397.20 | 2757.92 ± 918.96 |
| $AUC_{0-\infty}$ (ng · h/mL) | 3495.31 ± 1425.30 | 3313.94 ± 1684.18 | 3836.32 ± 1439.69 | 2779.79 ± 924.38 |
| AUC % | 0.73 ± 0.42 | 1.70 ± 1.44 | 0.87 ± 0.65 | 0.81 ± 0.23 |
| $\lambda_z$ (1/h) | 0.0906 ± 0.0300 | 0.0781 ± 0.0431 | 0.0998 ± 0.0242 | 0.0819 ± 0.0289 |
| $T_{1/2}$ (h) | 8.70 ± 4.06 | 11.90 ± 7.60 | 7.54 ± 2.95 | 9.40 ± 3.24 |
| CL/F (L/h) | 19.42 ± 6.60 | 21.33 ± 8.06 | 17.33 ± 5.40 | 24.20 ± 9.42 |
| Vz/F (L) | 249.10 ± 161.40 | 404.03 ± 405.78 | 176.59 ± 47.48 | 301.18 ± 77.01 |

[a]Median (range)

Differences in median $T_{max}$ for participants with mild, moderate, or severe hepatic impairment as compared with participants with normal hepatic function were 0 hr, 0.25 hr, and 0.75 hr, respectively. The mean terminal elimination half life of atogepant was generally similar in participants with hepatic impairment and in participants with normal hepatic function.

Table 8 provides a statistical comparison of the PK parameters for participants with varying degrees of hepatic impairment and participants with normal hepatic function including the ratio of geometric means and 90% CI.

TABLE 8

Summary of Statistical Analysis of Plasma Atogepant PK Parameters Following Single Dose Oral Administration of 60 mg Atogepant in Participants with Mild, Moderate, or Severe Hepatic Impairment (test) as Compared with Participants with Normal Hepatic Function (reference), PK Population

| Hepatic | PK | Geometric Least Squares Mean | | Ratio of Geometric Means | 90% | 90% |
|---|---|---|---|---|---|---|
| Group | Parameter | Test | Reference | Test/Reference | Lower CI | Upper CI |
| Mild Impairment | $C_{max}$ (ng/mL) | 586.89 | 538.55 | 108.97 | 72.72 | 163.31 |
| | $AUC_{0-t}$ (ng · h/mL) | 3249.63 | 2612.14 | 124.40 | 89.78 | 172.38 |
| | $AUC_{0-\infty}$ (ng · h/mL) | 3273.58 | 2633.43 | 124.31 | 89.83 | 171.83 |

TABLE 8-continued

Summary of Statistical Analysis of Plasma Atogepant PK Parameters Following Single Dose Oral Administration of 60 mg Atogepant in Participants with Mild, Moderate, or Severe Hepatic Impairment (test) as Compared with Participants with Normal Hepatic Function (reference), PK Population

| Hepatic Group | PK Parameter | Geometric Least Squares Mean Test | Reference | Ratio of Geometric Means Test/Reference | 90% Lower CI | 90% Upper CI |
|---|---|---|---|---|---|---|
| Moderate Impairment | $C_{max}$ (ng/mL) | 474.85 | 538.55 | 88.17 | 58.83 | 132.14 |
| | $AUC_{0-t}$ (ng · h/mL) | 2976.87 | 2612.14 | 113.96 | 82.25 | 157.91 |
| | $AUC_{0-\infty}$ (ng · h/mL) | 3028.57 | 2633.43 | 115.00 | 83.20 | 158.97 |
| Severe Impairment | $C_{max}$ (ng/mL) | 515.45 | 538.55 | 95.71 | 63.86 | 143.44 |
| | $AUC_{0-t}$ (ng · h/mL) | 3601.63 | 2612.14 | 137.88 | 99.51 | 191.05 |
| | $AUC_{0-\infty}$ (ng · h/mL) | 3633.22 | 2633.43 | 137.97 | 99.81 | 190.71 |

Participants with mid hepatic impairment had 9% higher $C_{max}$ and 24% higher AUC when compared with participants with normal hepatic function after administration of a single oral dose of 60 mg atogepant. Participants with moderate hepatic impairment had a 12% lower $C_{max}$ but 14%-15% higher AUC; while those with severe hepatic impairment showed a decrease of 4% in atogepant $C_{max}$ with a 38% increase in atogepant AUC, as compared with participants with normal hepatic function.

Protein binding blood samples were collected from all participants starting on Day 1 at 0 hour (predose) and at 2 hours post dose. The pre-dose samples collected prior to dosing for each participant were externally spiked with known quantities of atogepant. Percent bound atogepant was determined in the 2-hour sample using direct measurement of the atogepant concentrations in the blood sample. Percentage of bound atogepant is summarized in Table 9.

TABLE 9

Summary of Atogepant Plasma Protein-Binding (Expressed as Percent Bound) in Participants with Mild, Moderate, or Severe Hepatic Impairment and in Participants with Normal Hepatic Function Following Single Dose Oral Administration of 60 mg Atogepant, PK Population

| Hepatic Group | 0 hr (Predose) | 2 hr |
|---|---|---|
| Mild-impaired (N = 8) | 97.03 ± 0.75 | 97.36 ± 0.70 |
| Moderate-Impaired (N = 8) | 96.60 ± 0.94 | 97.05 ± 0.62 |
| Severe-Impaired (N = 8) | 94.48 ± 1.21 | 95.34 ± 0.85 |
| Normal Hepatic Function (N = 8) | 97.89 ± 0.54 | 98.21 ± 0.46 |

Plasma protein binding did not change substantially in participants with impaired hepatic function when compared with participants with normal hepatic function. In participants with mild, moderate, or severe hepatic impairment administered a single oral dose of 60 mg atogepant, percentage of plasma protein-bound atogepant was 97.4%, 97.1%, and 95.3%, respectively, as compared with 98.2% in participants with normal hepatic function. Plasma protein binding was generally similar across all hepatic-impairment groups as well as in participants with normal hepatic function.

Overall, there was no clinically relevant change in the PK of atogepant in participants with mild, moderate, or severe hepatic impairment. Compared with participants with normal hepatic function, the maximum plasma concentrations of atogepant were generally unchanged in participants with mild, moderate, or severe hepatic impairment (+9%, −12%, and −4%, respectively). The overall extent of atogepant systemic exposures (AUC) were slightly higher (14% to 38%) in participants with hepatic impairment as compared with participants with normal hepatic function, but these changes are unlikely to be clinically relevant.

Atogepant was well tolerated by participants in all hepatic function groups. One AE was reported during this study, which was mild and transient. No SAEs or AEs leading to premature discontinuation were reported and no participants died. No clinically relevant changes in clinical laboratory parameters, vital signs, or ECG values were observed in any hepatic function group. No participant met the potential Hy's law criteria. No safety concerns were identified relative to administration of a single 60-mg dose of atogepant to participants with hepatic impairment.

Example 4

Population pharmacokinetic modeling was conducted to evaluate the co-administration of atogepant with moderate CYP3A4 inhibitors (e.g., cyclosporine, ciprofloxacin, fluconazole, fluvoxamine, grapefruit juice) or weak CYP3A4 inhibitors (e.g., cimetidine, esomeprazole). Modeling suggested that moderate CYP3A4 inhibitors increase atogepant AUC by 1.7-fold, and that mild CYP3A4 inhibitors increase atogepant AUC by 1.1-fold. The changes in atogepant exposure when co-administered with weak or moderate CYP3A4 inhibitors are not expected to be clinically significant.

Example 5

A phase 1, open-label, 2-intervention, single-sequence, nonrandomized, crossover, drug-drug interaction study was conducted to evaluate the effects of multiple-dose esomeprazole magnesium 40 mg on pharmacokinetics (PK) and safety of co-administered single-dose atogepant 60 mg in healthy adults.

In this study, healthy adult participants received single-dose oral atogepant 60 mg on day 1, followed by once-daily esomeprazole 40 mg on days 7-13, co-administered with single-dose atogepant on day 12. Samples for atogepant PK analysis were collected on days 1 and 12. PK parameters calculated from atogepant plasma concentrations included peak plasma concentration ($C_{max}$); time to $C_{max}$ ($t_{max}$); area under plasma concentration-time curve from time 0 to time 5 ($AUC_{0-t}$) and from time 0 to infinity ($AUC_{0-\infty}$). PK parameters of atogepant alone vs. co-administered with esomeprazole were compared using a mixed-effects model. Statistical significance was achieved if 90% confidence intervals (CIs) for geometric least squares mean ratios (GMRs) of PK parameter values for atogepant co-administered with esomeprazole to atogepant administered alone were within 80%-125%.

Thirty-two participants (mean age 30.8 years; 50% male) were enrolled; 29 (90.6%) completed the study. Median plasma atogepant $t_{max}$ was delayed 1.5 hours, from 1.51 hours for atogepant alone to 3.00 hours for coadministration with esomeprazole. GMRs (90% CI) were 76.63 (69.19-86.11) for $C_{max}$; 91.61 (93.67-100.29) for $AUC_{0-t}$; and 92.04 (94.12-100.71) for $AUC_{0-\infty}$; only the change in $C_{max}$ was statistically significant. Treatment-emergent adverse events were generally infrequent and mild in intensity, except one event each of presyncope (moderate) and elective abortion (severe).

Coadministration with esomeprazole reduced the rate (23% reduced $C_{max}$; increased $t_{max}$) but not the extent of atogepant absorption; this interaction is unlikely to have clinical significance. Atogepant 60 mg alone or co-administered with esomeprazole magnesium 40 mg was safe and tolerated in healthy participants.

Example 6

A phase 1, single-center, single-sequence, open-label, 2-intervention, drug-drug interaction study was conducted to evaluate the effects of P-glycoprotein (P-gp) inhibition by quinidine gluconate on pharmacokinetics (PK) and safety of atogepant. In this study, healthy adults received atogepant 60 mg on day 1, quinidine gluconate 324 mg twice daily on Day 8, quinidine gluconate 648 mg twice-daily on days 9-12, and atogepant 60 mg co-administered on day 11. Plasma samples were collected on days 1 and 11.

Atogepant PK parameters calculated were peak plasma concentration ($C_{max}$); time to $C_{max}$ ($t_{max}$); and area under plasma concentration–time curve from time 0 to time t ($AUC_{0-t}$) and infinity ($AUC_{0-\infty}$). PK parameters of atogepant co-administered with quinidine gluconate vs. atogepant administered alone were compared using a mixed-effects model. Statistical significance was achieved if 90% confidence intervals (Cis) for least squares geometric mean ratios (GMRs) of PK parameter values for atogepant co-administered with quinidine gluconate to atogepant administered alone were within 80%-125%. Safety assessments included clinical laboratory values, vital signs, electrocardiograms, and treatment-related adverse events (TEAEs).

Of 33 enrolled participants (mean age 30.3 years, 72.7% males), 23 (69.7%) completed the study. 10 discontinued because of treatment-emergent adverse events (TEAEs; all electrocardiogram QT prolongation during quinidine gluconate administration). Atogepant median $t_{max}$ was 1.50 hours with or without quinidine gluconate administration. GMRs (90% CI) were 104.41 (89.17-122.25) for $C_{max}$, 120.49 (110.21-142.88) for $AUC_{0-t}$, and 125.91 (110.56-143.40) for $AUC_{0-\infty}$; changes in AUC were statistically significant. TEAEs were mostly related to quinidine gluconate administration.

Atogepant $C_{max}$ increased 4.4% and AUC increased approximately 25% when co-administered with quinidine gluconate. However, these changes are not expected to be clinically significant. Atogepant 60 mg was safe and well tolerated when administered alone or co-administered with quinidine gluconate in healthy participants.

Example 7

The efficacy of atogepant for the preventive treatment of episodic migraine in adults was demonstrated in two randomized, multicenter, double-blind, placebo-controlled studies (Study 1 and Study 2). The studies enrolled patients with at least a 1-year history of migraine with or without aura, according to the International Classification of Headache Disorders (ICHD-3) diagnostic criteria.

In Study 1 (NCT03777059), 910 patients were randomized 1:1:1:1 to receive atogepant 10 mg (N=222), atogepant 30 mg (N=230), atogepant 60 mg (N=235), or placebo (N=223), once daily for 12 weeks. In Study 2 (NCT02848326), 652 patients were randomized 1:2:2:2 to receive atogepant 10 mg (N=94), atogepant 30 mg (N=185), atogepant 60 mg (N=187), or placebo (N=186), once daily for 12 weeks. In both studies, patients were allowed to use acute headache treatments (i.e., triptans, ergotamine derivatives, NSAIDs, acetaminophen, and opioids) as needed. The use of a concomitant medication that acts on the CGRP pathway was not permitted for either acute or preventive treatment of migraine. The studies excluded patients with myocardial infarction, stroke, or transient ischemic attacks within six months prior to screening.

Study 1

The primary efficacy endpoint was the change from baseline in mean monthly migraine days (MMD) across the 12-week treatment period. Secondary endpoints included the change from baseline in mean monthly headache days, the change from baseline in mean monthly acute medication use days, the proportion of patients achieving at least a 50% reduction from baseline in mean MMD (3-month average), the change from baseline in mean monthly Activity Impairment in Migraine-Diary (AIM-D) Performance of Daily Activities (PDA) domain scores, the change from baseline in mean monthly AIM-D Physical Impairment (PI) domain scores, across the 12 week treatment period, and the change from baseline at Week 12 for Migraine Specific Quality of Life Questionnaire version 2.1 (MSQ v2.1) Role Function-Restrictive (RFR) domain scores.

The AIM-D evaluates difficulty with performance of daily activities (PDA domain) and physical impairment (PI domain) due to migraine, with scores ranging from 0 to 100. Higher scores indicate greater impact of migraine, and reductions from baseline indicate improvement. The MSQ v2.1 Role Function-Restrictive (RFR) domain score assesses how often migraine impacts function related to daily social and work-related activities over the past 4 weeks, with scores ranging from 0 to 100. Higher scores indicate lesser impact of migraine on daily activities, and increases from baseline indicate improvement.

Patients had a mean age of 42 years (range 18 to 73 years), 89% were female, 83% were White, 14% were Black, and 9% were of Hispanic or Latino ethnicity. The mean migraine frequency at baseline was approximately 8 migraine days per month and was similar across treatment groups. A total of 805 (88%) patients completed the 12-week double-blind study period. Key efficacy results of Study 1 are summarized in Table 10.

TABLE 10

| Efficacy Endpoints in Study 1 | Atogepant 10 mg N = 214 | Atogepant 30 mg N = 223 | Atogepant 60 mg N = 222 | Placebo N = 214 |
|---|---|---|---|---|
| Monthly Migraine Days (MMD) across 12 weeks | | | | |
| Baseline | 7.5 | 7.9 | 7.8 | 7.5 |
| Mean change from baseline | −3.7 | −3.9 | −4.2 | −2.5 |
| Difference from placebo | −1.2 | −1.4 | −1.7 | |
| p-value | <0.001 | <0.001 | <0.001 | |
| Monthly Headache Days across 12 weeks | | | | |
| Baseline | 8.4 | 8.8 | 9.0 | 8.4 |
| Mean change from baseline | −3.9 | −4.0 | −4.2 | −2.5 |
| Difference from placebo | −1.4 | −1.5 | −1.7 | |
| p-value | <0.001 | <0.001 | <0.001 | |
| Monthly Acute Medication Use Days across 12 weeks | | | | |
| Baseline | 6.6 | 6.7 | 6.9 | 6.5 |
| Mean change from baseline | −3.7 | −3.7 | −3.9 | −2.4 |
| Difference from placebo | −1.3 | −1.3 | −1.5 | |
| p-value | <0.001 | <0.001 | <0.001 | |
| ≥50% MMD Responders across 12 weeks | | | | |
| % Responders | 56 | 59 | 61 | 29 |
| Difference from placebo (%) | 27 | 30 | 32 | |
| p-value | <0.001 | <0.001 | <0.001 | |
| MSQ v2.1 RFR Domain* at week 12 | | | | |
| Baseline | 44.9 | 44.0 | 46.8 | 46.8 |
| Mean change from baseline | 30.4 | 30.5 | 31.3 | 20.5 |
| Difference from placebo | 9.9 | 10.1 | 10.8 | |
| p-value | <0.001 | <0.001 | <0.001 | |
| AIM-D PDA Domain** across 12 weeks | | | | |
| Baseline | 15.5 | 16.9 | 15.9 | 15.2 |
| Mean change from baseline | −7.3 | −8.6 | −9.4 | −6.1 |
| Difference from placebo | −1.2 | −2.5 | −3.3 | |
| p-value | NS† | <0.001 | <0.001 | |
| AIM-D PI Domain*** across 12 weeks | | | | |
| Baseline | 11.7 | 13.0 | 11.6 | 11.2 |
| Mean change from baseline | −5.1 | −6.0 | −6.5 | −4.0 |
| Difference from placebo | −1.1 | −2.0 | −2.5 | |
| p-value | NS† | 0.002 | <0.001 | |

*Migraine Specific Quality of Life Questionnaire version 2.1 Role Function-Restrictive domain score
**Activity Impairment in Migraine-Diary Performance of Daily Activities domain score
***Activity Impairment in Migraine-Diary Physical Impairment domain score
†Not statistically significant (NS)

Figure 6:
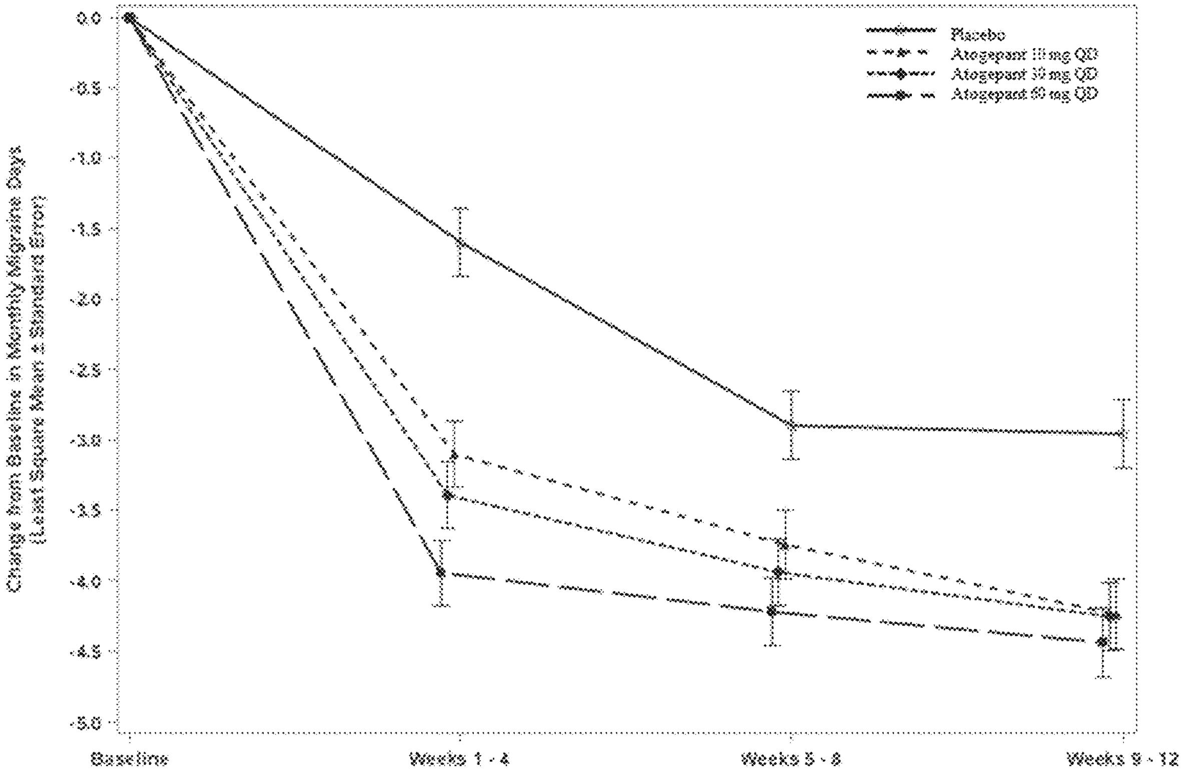
FIG. 6 shows the mean change from baseline in monthly migraine days in Study 1 (NCT03777059).
Figure 7:
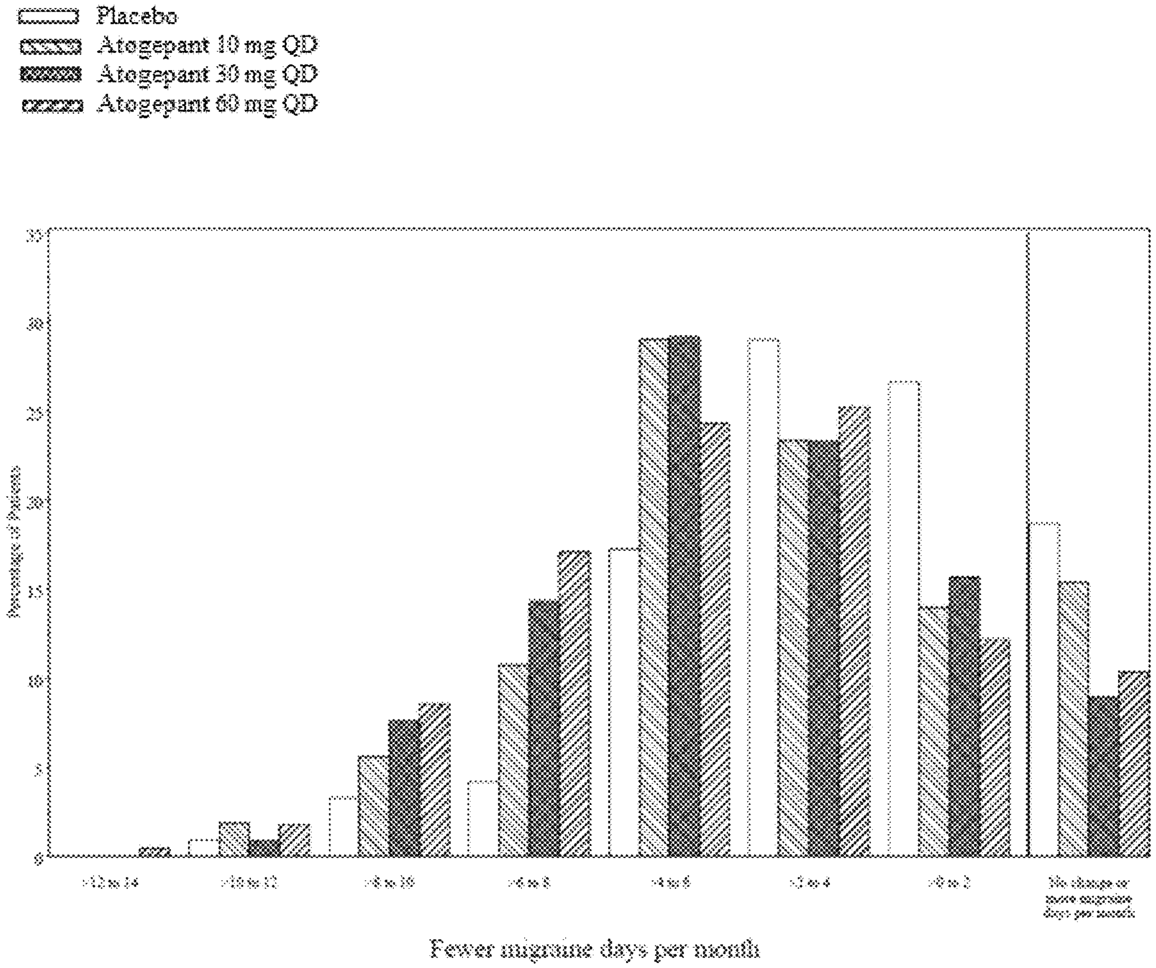
FIG. 7 shows the distribution of change from baseline in mean monthly migraine days (MMD) across the 12-week treatment period, in 2-day increments, by treatment group in Study 1.

The mean change from baseline in MMD in Study 1 is shown in FIG. 6. FIG. 7 shows the distribution of change from baseline in mean monthly migraine days (MMD) across the 12-week treatment period, in 2-day increments, by treatment group. A treatment benefit over placebo for all doses of atogepant is seen across a range of mean changes from baseline in MMD.

Study 2

The primary efficacy endpoint was the change from baseline in mean monthly migraine days across the 12-week treatment period.

Patients had a mean age of 40 years (range: 18 to 74 years), 87% were female, 76% were white, 20% were Black, and 15% were of Hispanic or Latino ethnicity. The mean migraine frequency at baseline was approximately 8 migraine days per month. A total of 541 (83%) patients completed the 12-week double-blind study period.

In Study 2, there was a significantly greater reduction in mean monthly migraine days across the 12-week treatment period in all three atogepant treatment groups, compared with placebo, as summarized in Table 11.

TABLE 11

| Efficacy Endpoints in Study 2 | Atogepant 10 mg N = 92 | Atogepant 30 mg N = 182 | Atogepant 60 mg N = 177 | Placebo N = 178 |
|---|---|---|---|---|
| Monthly Migraine Days (MMD) across 12 weeks | | | | |
| Baseline | 7.6 | 7.6 | 7.7 | 7.8 |
| Mean change from baseline | −4.0 | −3.8 | −3.6 | −2.8 |
| Difference from placebo | −1.1 | −0.9 | −0.7 | |
| p-value | 0.024 | 0.039 | 0.039 | |
| Monthly Headache Days across 12 weeks | | | | |
| Baseline | 8.9 | 8.7 | 8.9 | 9.1 |
| Mean change from baseline | −4.3 | −4.2 | −3.9 | −2.9 |
| Difference from placebo | −1.4 | −1.2 | −0.9 | |
| p-value | 0.024 | 0.039 | 0.039 | |

Figure 8:
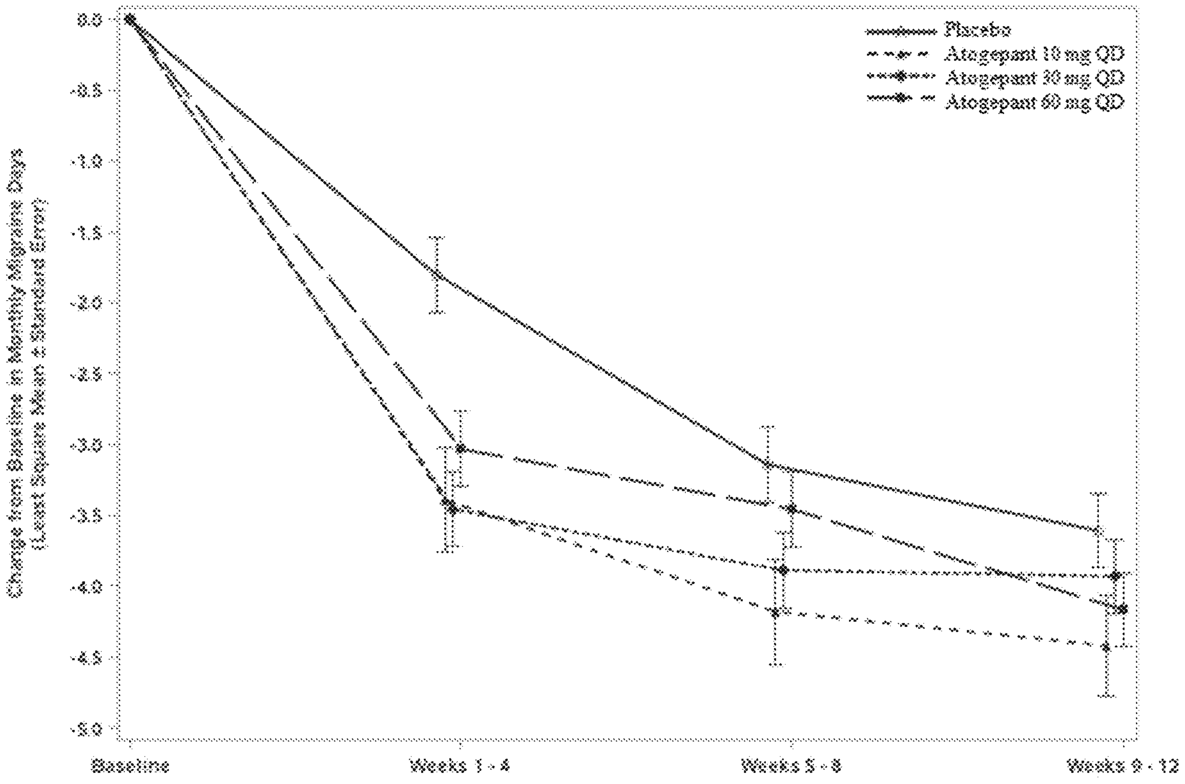
FIG. 8 shows the mean change from baseline in MMD in Study 2 (NCT02848326).

FIG. 8 shows the mean change from baseline in MMD in Study 2. Patients treated with atogepant had greater mean decreases from baseline in MMD across the 12-week treatment period compared to patients who received placebo.

Figure 9:
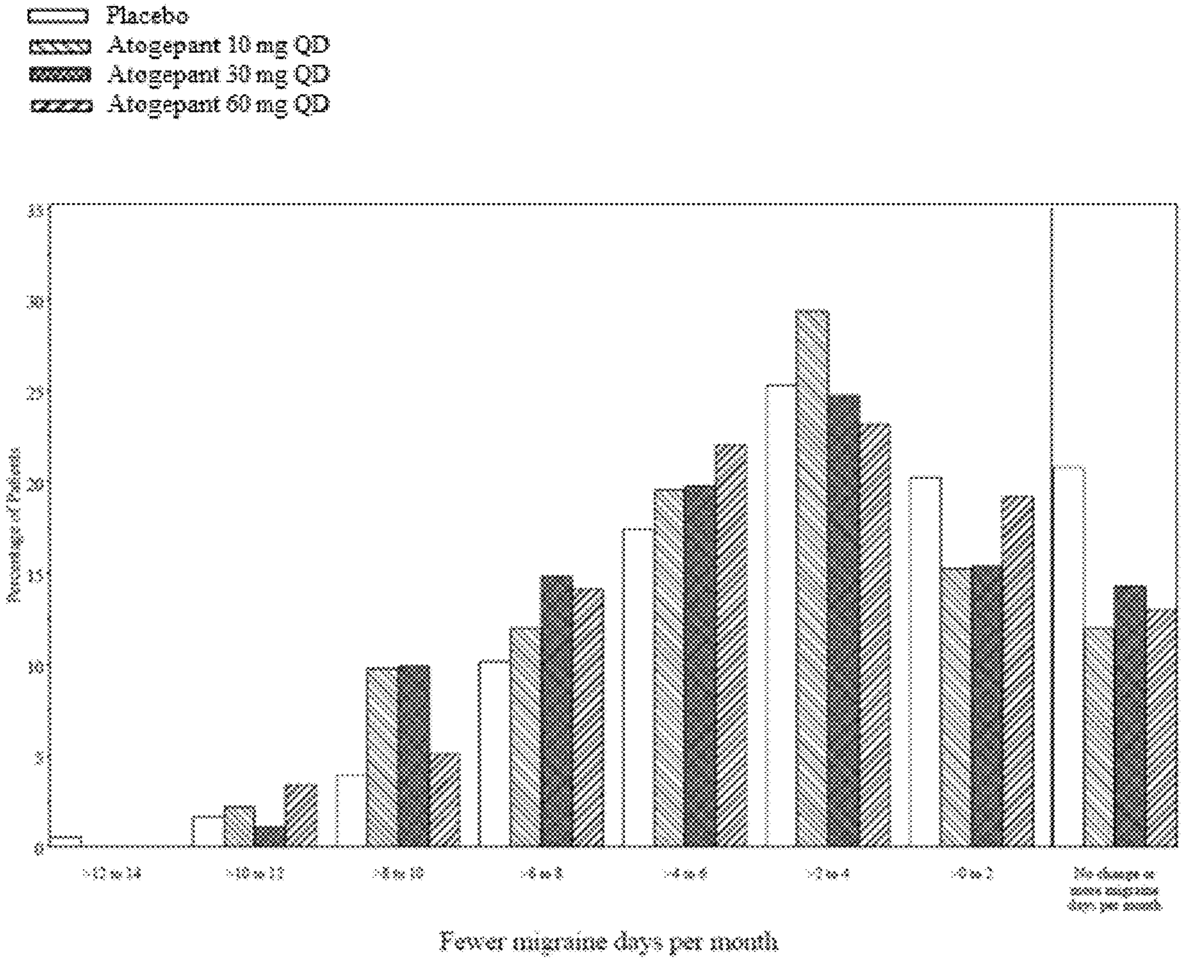
FIG. 9 shows the distribution of change from baseline in mean MMD across the 12-week treatment period, in 2-day increments, by treatment group in Study 2. A treatment benefit over placebo for all doses of atogepant is seen across a range of mean changes from baseline in MMD.

FIG. 9 shows the distribution of change from baseline in mean MMD across the 12-week treatment period, in 2-day increments, by treatment group. A treatment benefit over placebo for all doses of atogepant is seen across a range of mean changes from baseline in MMD.

Example 8

The safety of atogepant was evaluated in 1958 patients with migraine who received at least one dose of atogepant. Of these, 839 patients were exposed to atogepant once daily for at least 6 months, and 487 patients were exposed for 12 months. In the 12-week, placebo-controlled clinical studies (Study 1 and Study 2, discussed above in Example 7), 314 patients received at least one dose of atogepant 10 mg once daily, 411 patients received at least one dose of atogepant 30 mg once daily, 417 patients received at least one dose of atogepant 60 mg once daily, and 408 patients received placebo. Approximately 88% were female, 80% were White, 17% were Black, and 12% were of Hispanic or Latino ethnicity. The mean age at study entry was 41 years (range 18 to 74 years).

The most common adverse reactions (incidence at least 4% and greater than placebo) are nausea, constipation, and fatigue.

Table 12 summarizes the adverse reactions that occurred during Study 1 and Study 2.

TABLE 12

Adverse Reactions Occurring with an Incidence of at least 2% for Atogepant and Greater than Placebo in Studies 1 and 2

| | Placebo (N = 408) % | Atogepant 10 mg (N = 314) % | Atogepant 30 mg (N = 411) % | Atogepant 60 mg (N = 417) % |
|---|---|---|---|---|
| Nausea | 3 | 5 | 6 | 9 |
| Constipation | 1 | 6 | 6 | 6 |
| Fatigue/Somnolence | 3 | 4 | 4 | 6 |
| Decreased Appetite | <1 | 2 | 1 | 2 |

The adverse reactions that most commonly led to discontinuation in Studies 1 and 2 were constipation (0.5%), nausea (0.5%), and fatigue/somnolence (0.5%).

Liver Enzyme Elevations

In Study 1 and Study 2, the rate of transaminase elevations over 3 times the upper limit of normal was similar between patients treated with atogepant (1.0%) and those treated with placebo (1.8%). However, there were cases with transaminase elevations over 3 times the upper limit of normal that were temporally associated with atogepant treatment; these were asymptomatic, and resolved within 8 weeks of discontinuation. There were no cases of severe liver injury or jaundice.

Decreases in Body Weight

In Studies 1 and 2, the proportion of patients with a weight decrease of at least 7% at any point was 2.8% for placebo, 3.8% for atogepant 10 mg, 3.2% for atogepant 30 mg, and 4.9% for atogepant 60 mg.

Example 9

A single-center, randomized, open-label, single-dose, 2-period cross-over study was conducted to evaluate the effect of a high-fat meal on the systemic exposure of atogepant following single-dose administration of an immediate release (IR) tablet in healthy adult participants. Secondary objectives were to evaluate the secondary PK parameters of atogepant following single-dose administration of an IR tablet formulation of atogepant in healthy participants under fasted and fed conditions; and to evaluate the safety and tolerability profiles of single-dose atogepant in healthy adult participants under fed and fasted conditions.

Twenty healthy adult male and female participants, aged 18-45 years, received a single 60 mg dose of atogepant after an overnight fast or following a high-fat meal (served 30 minutes prior to dosing) with a washout period of 7 days between interventions. Plasma samples were collected predose and at predetermined time intervals up to 48 hours after dosing. Atogepant plasma concentrations were determined using a validated LC-MS/MS assay and the pharmacokinetic (PK) parameters were calculated using WinNonlin. A linear mixed-effects model with sequence, study intervention, and period as fixed effects, and participant nested within sequence as a random effect was used to compare the natural logarithm transformed values of atogepant PK parameters $AUC_{0\text{-}t}$, $AUC_{0\text{-}inf}$, and $C_{max}$. Safety was monitored via ECGs, vital signs, clinical labs, and adverse events.

Participants were randomly assigned to receive Study Intervention A (single dose of 60-mg atogepant, IR formulation, 1×60 mg atogepant tablet; fed conditions) or Study Intervention B (single dose of 60-mg atogepant, IR formulation, 1×60 mg atogepant tablet; fasted conditions).

Screening occurred within 21 days before dosing (Days −21 to −1). The study intervention period was scheduled for a total of 11 days (Days −1 to 10), and the follow-up visit occurred with serum chemistry on day 38 (±3), (30 [±3] days after the last dose on Day 8). PK blood samples for analysis of plasma atogepant concentrations were collected starting on Days 1 (period 1) and 8 (period 2); at 0 hour (predose) and 0.5, 1, 1.5, 2, 3, 4, 6, 8, 12, 16, 24, 36, and 48 hours postdose.

Overall, 20 participants were randomly assigned to receive Study Interventions A and B in 1 of 2 sequences, with a washout period of at least 7 days between each study intervention, as shown in Table 13. Nineteen (95.0%) participants completed the study and 1 (5.0%) participant was discontinued from the study on Day 7 (period 2) due to a significant protocol deviation.

TABLE 13

Study Intervention Sequences

| | Period 1 | Period 2 |
|---|---|---|
| Sequence I | Study Intervention A | Study Intervention B |
| Sequence II | Study Intervention B | Study Intervention A |

Study Intervention A: Single Dose of 60-mg atogepant, immediate release formulation (1×60 mg atogepant tablet), fed conditions.

Study Intervention B: Single Dose of 60-mg atogepant, immediate release formulation (1×60 mg atogepant tablet), fasted conditions.

Participants were healthy, male or female, aged 18 through 45 years, inclusive, with a body mass index ≥18 and ≤30 kg/m$^2$, and sitting pulse rate ≥40 and ≤100 bpm during the vital sign assessment at the Screening Visit. Participants must also have been nonsmoking and a nonuser of nicotine-containing products (never smoked or used nicotine-containing products or have not smoked or used nicotine-containing products, including eCigarettes, within the previous 6 months before study intervention administration). Twenty healthy participants with a mean age of 31.9 years (range: 23 to 44 years) were enrolled. The majority of participants were male (13 of 20 participants, 65.0%). Participants were black or African American (11 of 20 participants, 55.0%), white (8 of 20 participants, 40.0%), and of multiple races (1 of 20 participants, 5.0%). The mean (SD) weight was 72.95 (9.264) kg and mean (SD) body mass index was 24.15 (2.368) kg/m$^2$. Demographic and baseline characteristics were comparable across sequences, and the same for the PK and safety populations.

Atogepant plasma concentration data were analyzed for 19 and 20 participants for the fed and fasted study interventions, respectively.

Figure 10:
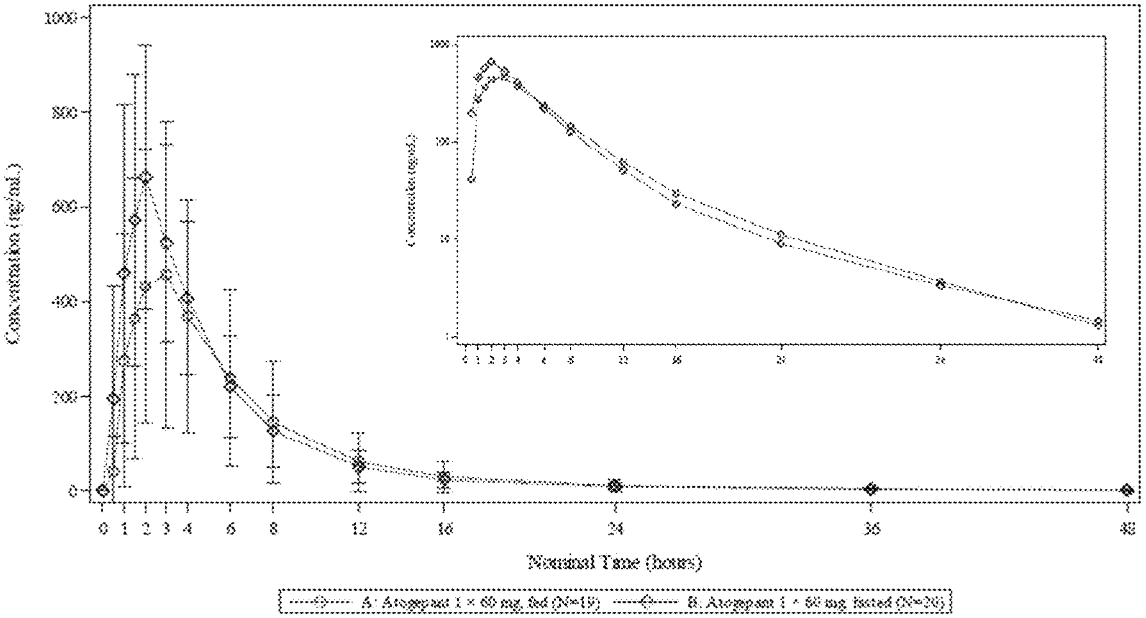
FIG. 10 provides the mean concentration-time profiles for plasma atogepant after single dose administration of a 1×60 mg atogepant IR tablet formulation under fed conditions and under fasted conditions (linear scale±SD, with semilogarithmic scale insert).
Figure 11:
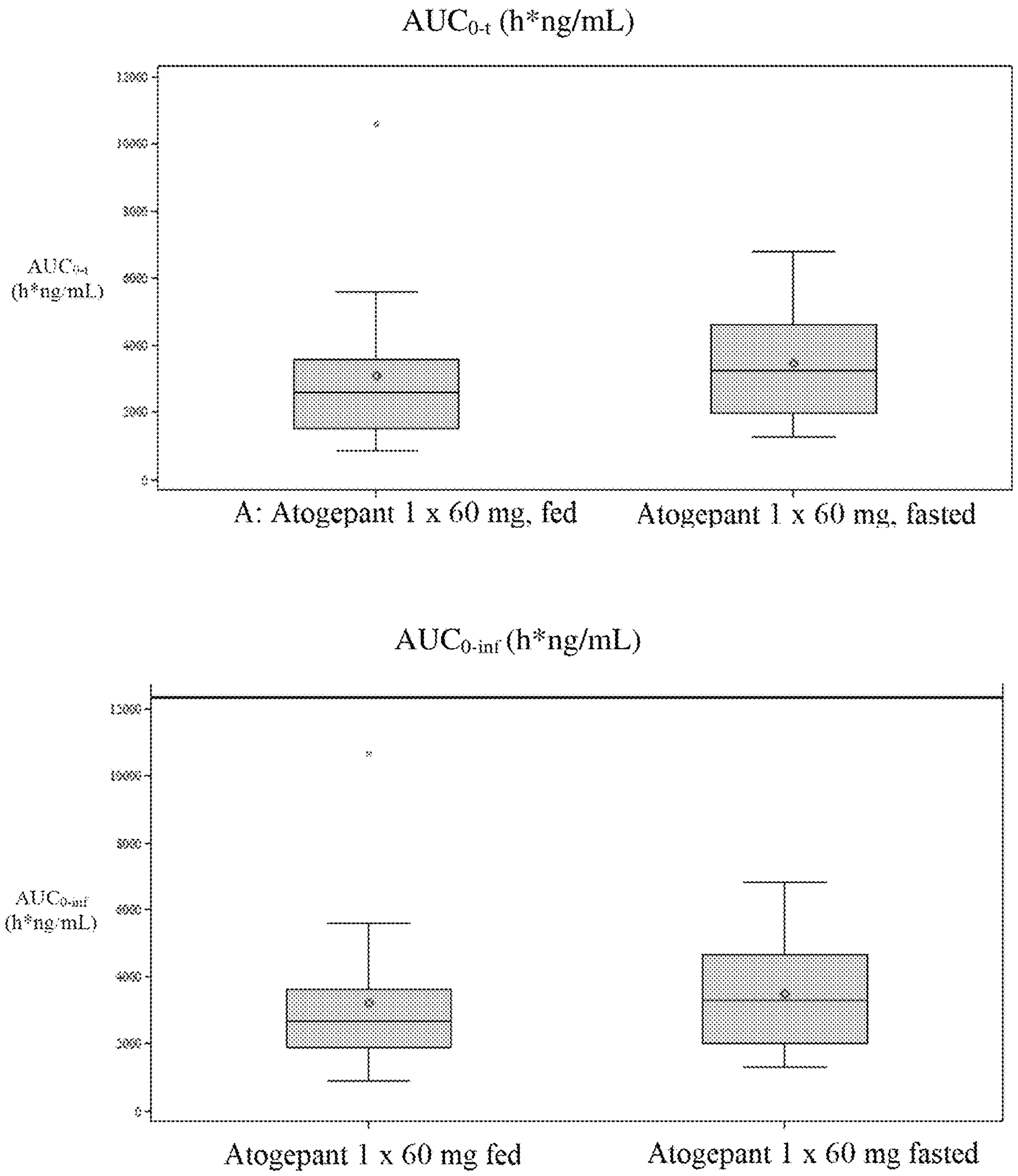
FIG. 11 provides boxplots of $AUC_{0-t}$ and $AUC_{0-inf}$ after single dose administration of a 1×60 mg atogepant IR tablet formulation under fed conditions and under fasted conditions.
Figure 12:
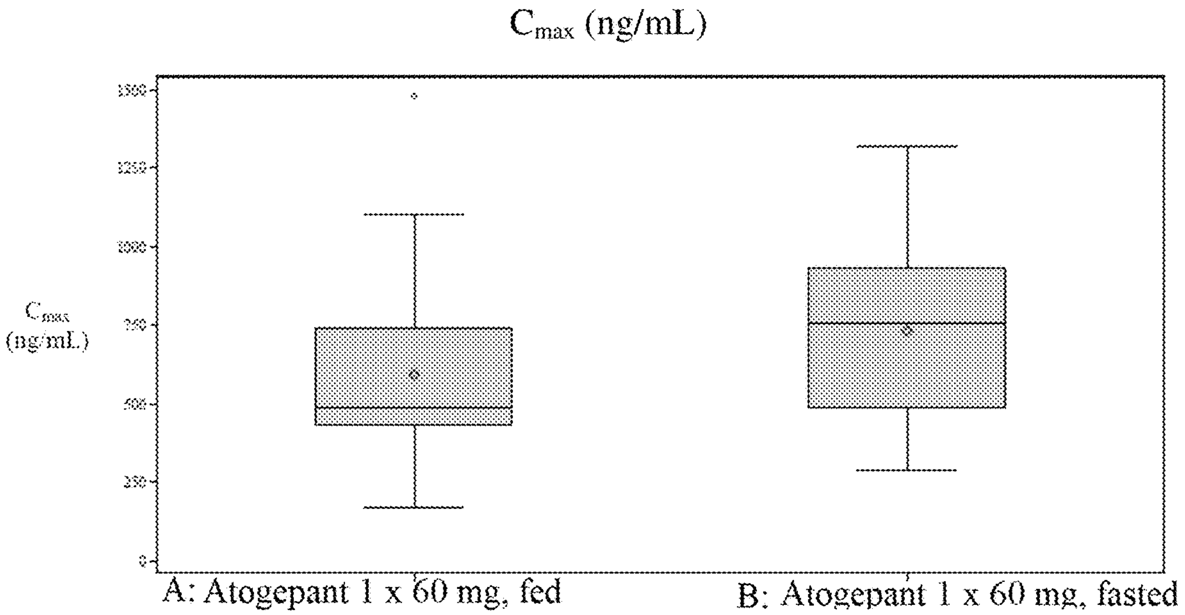
FIG. 12 provides a boxplot of $C_{max}$ after single dose administration of a 1×60 mg atogepant IR tablet formulation under fed conditions and under fasted conditions.

The mean concentration-time profiles for plasma atogepant after single-dose administration of the 1×60 mg atogepant IR formulation under fed conditions (Study Intervention A) and under fasted conditions (Study Intervention B) are presented in FIG. 10 (linear scale±SD, with semi-logarithmic scale insert). Plasma atogepant PK parameters are summarized in Table 14. Although mean $C_{max}$ and AUC were lower for atogepant administered under fed conditions than under fasted conditions, median $T_{max}$ and $T_{lag}$ values were the same and mean $t_{t1/2}$, CL/F, and $V_z$/F were similar for the two study interventions. Boxplots of plasma atogepant PK parameters are presented in FIG. 11 ($AUC_{0-t}$ and $AUC_{0-inf}$) and FIG. 12 ($C_{max}$).

TABLE 14

Mean (SD) Plasma Atogepant PK Parameters (PK Population)

| Parameter | Study Intervention A: Atogepant 1 × 60 mg, Fed (N = 19[a]) | Study Intervention B: Atogepant 1 × 60 mg, Fasted (N = 20) |
|---|---|---|
| $AUC_{0-t}$ (h*ng/mL) | 3088.54 (2207.78) | 3460.48 (1564.37) |
| $AUC_{0-inf}$ (h*ng/mL) | 3204.51 (2246.31) N = 18 | 3486.77 (1568.33) |
| $C_{max}$ (ng/mL) | 593.75 (309.74) | 731.64 (288.61) |
| $T_{max}$[b] | 2.01 (1.01-6.01) | 2.01 (1.01-4.01) |
| $T_{lag}$[b] | 0.00 (0.00-1.01) | 0.00 (0.00-0.00) |
| $\lambda_z$ (1/h) | 0.0840 (0.02862) N = 18 | 0.0799 (0.02962) |
| $t_{t/2}$ (h) | 9.41 (4.13) N = 18 | 9.71 (3.30) |
| CL/F (L/h) | 26.10 (15.20) N = 18 | 21.03 (9.87) |
| $V_z$/F (L) | 368.01 (299.19) N = 18 | 298.95 (192.93) |

[a]Unless otherwise indicated
[b]Median (minimum-maximum) reported for $T_{max}$ and $T_{lag}$

TABLE 15

Summary of Food-Effect Analysis (PK Population)

| Parameter (units) | Fed (Test) N | Fed (Test) GLSM | Fasted (Ref) N | Fasted (Ref) GLSM | Ratios of GLSMs (%) Test/Ref | Ratios of GLSMs (%) 90% CIs | Intra-CV % A (Test) | Intra-CV % B (ref) | Inter-CV % |
|---|---|---|---|---|---|---|---|---|---|
| $AUC_{0-t}$ (h*ng/mL) | 19 | 2558.05 | 20 | 3130.99 | 81.70 | 71.57-93.26 | 23.80[a] | | 50.29 |
| $AUC_{0-inf}$ (h*ng/mL) | 18 | 2606.55 | 20 | 3158.38 | 82.53 | 71.77-94.89 | 34.50 | 3.62 | 49.89 |
| $C_{max}$ (ng/mL) | 19 | 527.40 | 20 | 677.01 | 77.90 | 64.14 94.62 | 40.75 | 29.73 | 30.32 |

| Parameter (units) | Fed (Test) N | Fed (Test) Median | Fasted (ref) N | Fasted (ref) Median | Median of Paired Differences (Test Minus Reference) |
|---|---|---|---|---|---|
| Tmax (h) | 19 | 2.01 | 20 | 2.01 | 0.50 |

[a]Results for $AUC_{0-t}$ were provided from a model without the repeated statement (which allowed the variance of the response to vary across different study conventions), because the model did not converge.
GLSM = Geometric least Square Mean Linear mixed effects model with natural logarithm-transformed values of $AUC_{0-t}$, $AUC_{0-inf}$, and $C_{max}$, as the dependent variable and terms for study intervention, sequence, and period as fixed independent variables and participant nested in sequence as a random effect. The median of the difference in $T_{max}$ is also presented. Study intervention was a single dose of 60-mg atogepant immediate-release formulation (1×60-mg tablet) under fed and fasted conditions.

A food effect was demonstrated on the pharmacokinetics of atogepant 60-mg IR tablet formulation. The food effect, although statistically significant, was mild. Administration of the atogepant 60-mg IR tablet formulation under fed conditions reduced AUCs by approximately 18%, reduced $C_{max}$ by approximately 22% and, based on median paired differences, delayed $T_{max}$ by 0.5 hours compared with administration under fasted conditions. The mild food effect on atogepant PK is not considered clinically relevant.

Single doses of atogepant 60-mg IR formulation were safe and well-tolerated by the healthy participants in this study when administered under both fed and fasted conditions. No clinically meaningful differences in safety or tolerability were observed following administration of a single dose of 60-mg atogepant IR formulation under fed conditions as compared with fasted conditions.

Overall 7 (35.0%) participants experienced treatment emergent AEs (TEAEs). Of these, 3 (15%) participants had 4 TEAEs that were considered related to study intervention. The most frequently reported TEAEs were arthralgia and back pain (2 participants each, 10.0%). Of the 7 participants who reported TEAEs, 6 experienced TEAEs that were considered mild in severity and 1 participant experienced TEAEs of increased alanine aminotransferase and increased aspartate aminotransferase during follow-up that were considered moderate in severity, documented as adverse events of special interest, and considered not related to study intervention. There were no deaths or severe or serious TEAEs reported. No participants experienced TEAEs that led to study discontinuation. All TEAEs were recovered/resolved by the Follow-Up Visit.

Changes from baseline in mean clinical laboratory, vital sign, and safety 12-lead electrocardiogram (ECG) parameters were not clinically meaningful. Overall, 8 participants had potentially clinically significant laboratory values at end of dosing (EOD), and no participants had liver function test results that met criteria for a potential Hy's Law case. No participants had vital sign or 12-lead ECG results that met potentially clinically significant criteria during the study.

Example 10

Figure 13:
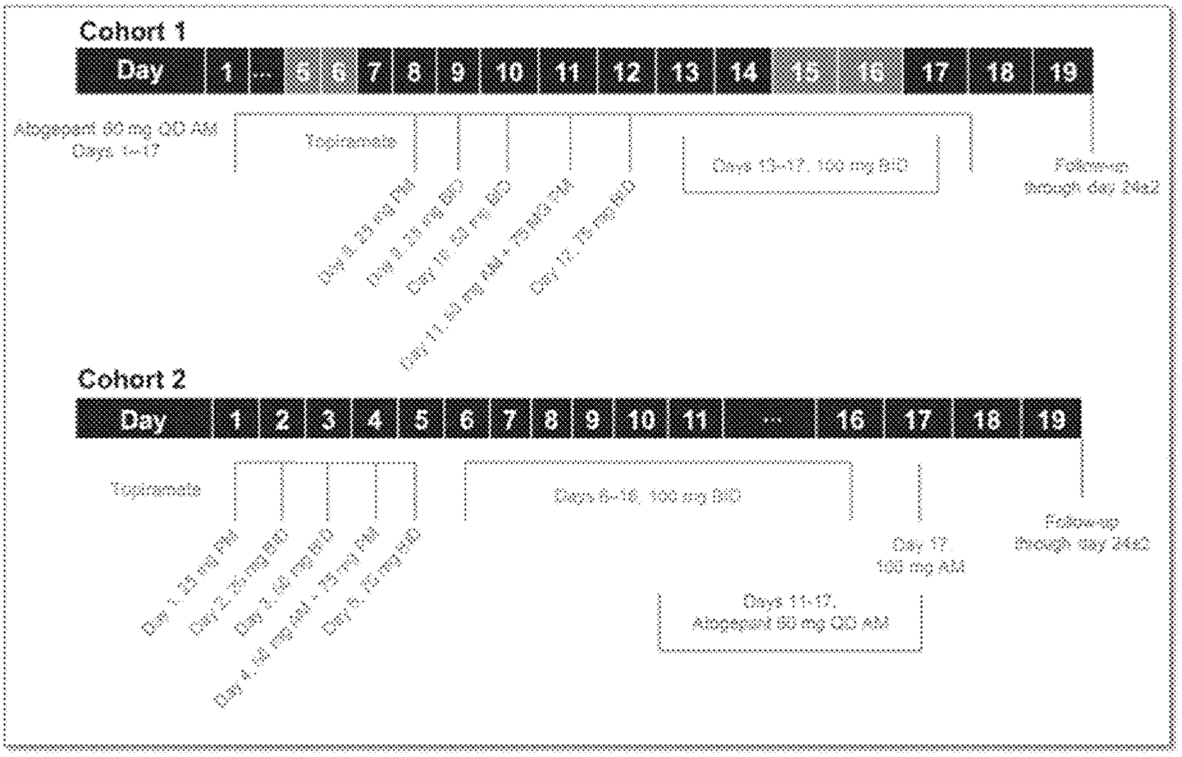
FIG. 13 provides the study design and dosing schedule for an open-label, single-center, multiple-dose 2-cohort, phase 1 trial to evaluate the potential DDI between atogepant and topiramate in healthy adult participants.

An open-label, single-center, multiple-dose 2-cohort, phase 1 trial was carried out to assess the potential of a PK DDI between atogepant and topiramate in healthy adult participants. Eligible participants were enrolled either in cohort 1 to evaluate the effect of topiramate 100 mg twice daily on the PK of atogepant 650 mg once daily or in cohort 2 to evaluate the effect of atogepant 60 mg once daily on the PK of topiramate 100 mg twice daily. Participants in cohort 1 received atogepant alone on days 1-7 and atogepant plus topiramate on days 8-17. Participants in cohort 2 received topiramate alone on days 1-10 and topiramate plus atogepant on days 11-17. The study design is set forth in FIG. 13.

The duration of the study was 25 days (±2 days), which included day −1 through the follow-up visit and excluded the screening period. The screening period was up to 21 days before day 1 and the intervention period was a total of 19 days, at which point the end of dosing visit was conducted. Cerebrospinal fluid (CSF) samples for measurement of atogepant concentration were collected via lumbar puncture in a subset of consenting participants in cohort 1. CSF samples were collected once from individual participants in the CSF collection subset at 2 or 6 hours after the morning dose on day 6 for cohort 1. Clinical laboratory tests were performed at the follow-up visit, which was conducted on day 24 (7 [±2] days after the last dose of study medication.

Eligible participants were healthy adults aged 18 to 45 years who were nonsmokers and had a body mass index between ≥18 and ≤30 kg/m2 and a sitting pulse rate between ≥45 and ≤100 beats per minute. Participants were excluded if they had clinically significant abnormal electrocardiogram (ECG) results or QT prolongation (QTcF≥450 msec for males, ≥470 for females), or any clinical condition or previous surgery that may affect the absorption, distribution, biotransformation, or excretion of atogepant or topiramate.

The primary endpoints were area under the plasma concentration-time curve during dosing interval at steady state ($AUC_{0\text{-}tau,ss}$) and maximum plasma drug concentration at steady state ($C_{max,ss}$) of atogepant and topiramate when coadministered and when administered alone. Additional PK parameters included time of maximum plasma drug concentration at steady state ($T_{max,ss}$), average plasma drug concentration at steady state ($C_{avg,ss}$), and minimum plasma drug concentration at steady state ($C_{min,ss}$) of topiramate and atogepant when coadministered and when administered alone. Safety and tolerability of atogepant, topiramate, and their combination were monitored throughout the study by clinical assessment of adverse events (AEs), measurement of vital signs, evaluation of 12-lead ECGs, and clinical laboratory tests (hematology, clinical chemistry, coagulation, and urinalysis) at specified time points.

The safety population included 28 participants in cohort 1 (28 received atogepant alone and 26 received atogepant plus topiramate; 24 participants were included in the CSF collection subset) and 25 participants in cohort 2 (25 received topiramate alone and 24 received topiramate plus atogepant). The PK analysis population for atogepant alone and atogepant plus topiramate included 25 and 21 participants, respectively. The PK analysis populations for topiramate alone and topiramate plus atogepant included 24 and 22 participants, respectively. A total of 21 participants in cohort 1 and 22 participants in cohort 2 completed the trial. Ten participants discontinued the trial: 8 participants due to AEs, 1 participant due to noncompliance with study drug, and 1 participant due to other reasons (noncompliance with study investigators). Baseline demographics were similar between the 2 cohorts, as shown in Table 16.

TABLE 16

Baseline Demographics

| | Cohort 1<br>n = 28 | Cohort 2<br>n = 25 |
|---|---|---|
| Age, mean (SD), years | 33.3 (6.2) | 33.6 (7.1) |
| Male, n (%) | 20 (71.4) | 20 (80.0) |
| Female, n (%) | 8 (28.6) | 5 (20.0) |
| Race, n (%) | | |
| White | 11 (39.3) | 7 (28.0) |
| Black or African American | 15 (53.6) | 16 (64.0) |
| BMI, mean (SD), kg/m$^2$ | 26.9 (2.3) | 25.3 (3.0) |

Abbreviations: BMI, body mass index; SD, standard deviation.

Figure 14:
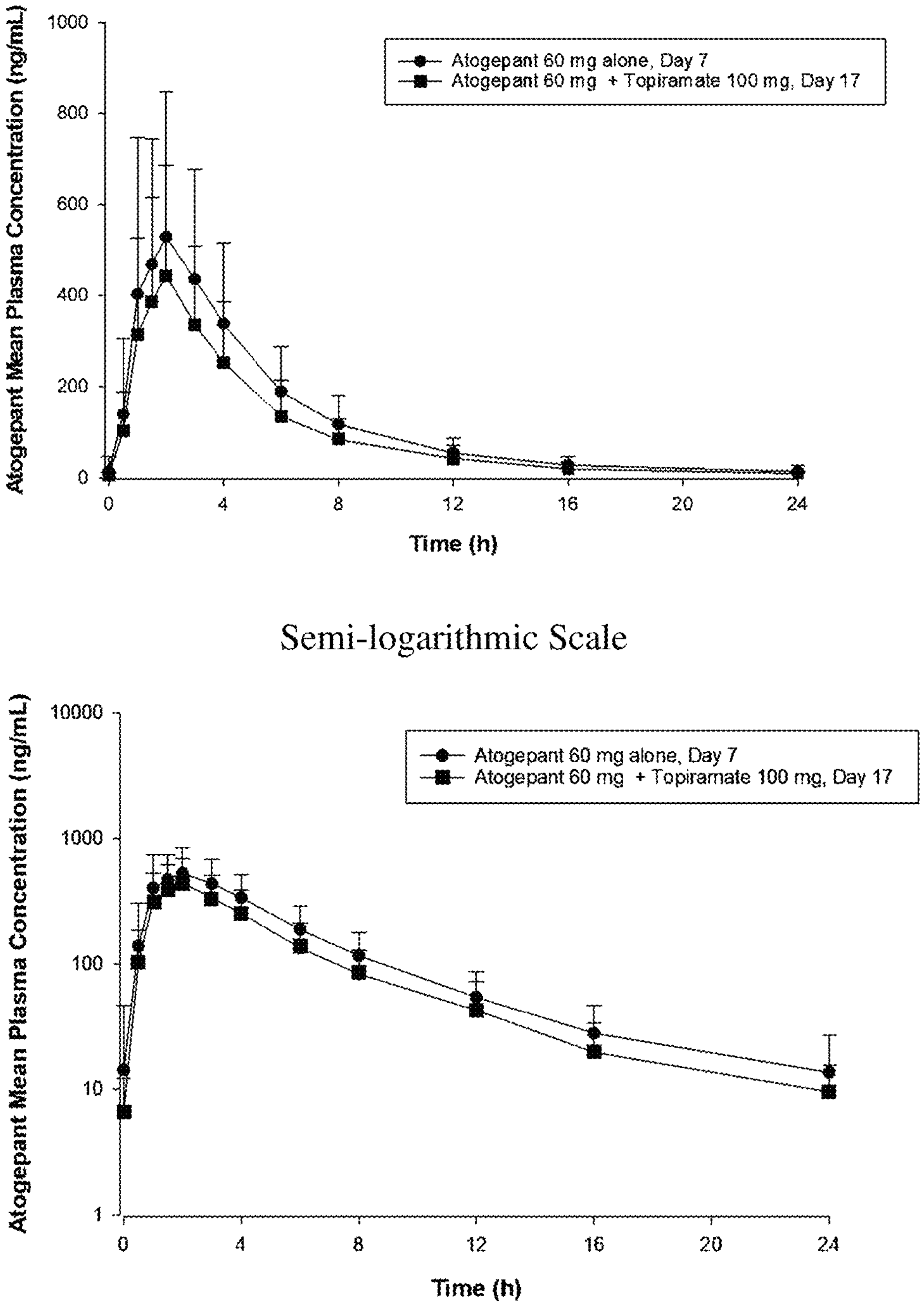
FIG. 14 shows the mean steady state plasma concentrations of atogepant following administration alone and in combination with topiramate in linear and semi-logarithmic scale.

The mean (standard deviation [SD]) steady state plasma concentrations of atogepant following administration alone and in combination with topiramate are shown in FIG. 14. These data demonstrate marginally lower atogepant plasma concentrations when atogepant was coadministered with topiramate compared with administration of atogepant alone. Table 17 summarizes the PK parameters of atogepant alone and in combination with topiramate. Coadministration of atogepant and topiramate reduced atogepant $C_{max,ss}$ compared with atogepant administered alone, while there was no change in the median $T_{max,ss}$.

TABLE 17

| Mean (±SD) PK parameters of atogepant alone (day 7) and in combination with topiramate (day 17) | | |
|---|---|---|
| PK Parameter | Atogepant 60 mg QD n = 25 | Atogepant 60 mg QD + Topiramate 100 mg BID n = 21 |
| $T_{max, ss}$ (h) | 2.0 (1-4)[a] | 2.0 (1-3)[a] |
| $C_{max, ss}$ (ng/mL) | 626.1 (376.9) | 491.4 (263.0) |
| $AUC_{0\text{-}tau, ss}$ (h · ng/mL) | 3015.4 (1477.0) | 2298.7 (1200.8) |
| $C_{min, ss}$ (ng/mL) | 10.2 (13.1) | 6.3 (4.9) |
| $C_{avg, ss}$ (ng/mL) | 125.6 (61.5) | 95.8 (50.0) |

[a]Median (min-max)

Abbreviations: $AUC_{0\text{-}tau, ss}$, area under the plasma concentration vs time curve during dosing interval at steady state; BID, twice daily; $C_{avg, ss}$, average plasma drug concentration at steady state; $C_{max, ss}$, maximum plasma drug concentration at steady state; $C_{min, ss}$, minimum plasma drug concentration at steady state; PK, pharmacokinetic; QD, once daily; SD, standard deviation; $T_{max, ss}$, time of maximum plasma drug concentration at steady state.

The analysis of GMRs showed that atogepant $AUC_{0\text{-}tau,ss}$ and $C_{max,ss}$ were reduced by 25% and 24%, respectively, when atogepant was coadministered with topiramate, as shown in Table 18. The GMR and lower 90% CI for both $AUC_{0\text{-}tau,ss}$ and $C_{max,ss}$ were below 0.80, suggesting a statistically significant reduction of atogepant exposure when coadministered with topiramate.

TABLE 18

| Statistical analysis of PK parameters: comparison of plasma atogepant alone and coadministered with topiramate | | | |
|---|---|---|---|
| Atogepant PK Parameter | Atogepant Alone Geometric LSM | Atogepant and Topiramate Geometric LSM | GMRs (90% CI) (Combination/Alone) |
| $AUC_{0\text{-}tau, ss}$ (h · ng/mL) | 2718.2 | 2026.4 | 0.75 (0.69, 0.81) |
| $C_{max, ss}$ (ng/mL) | 535.2 | 405.8 | 0.76 (0.68, 0.85) |

Abbreviations: $AUC_{0\text{-}tau, ss}$, area under the plasma concentration vs time curve during dosing interval at steady state; $C_{max, ss}$, maximum plasma drug concentration at steady state; CI, confidence interval; GMR, geometric mean ratio; LSM, least-square mean; PK, pharmacokinetic.

Figure 15:
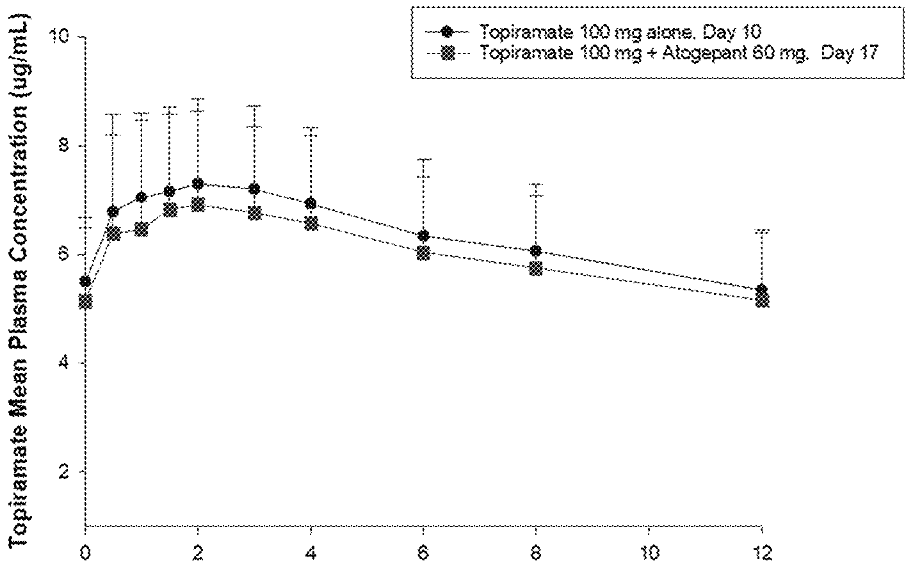
FIG. 15 shows mean (±SD) steady state plasma atogepant concentrations when administered alone and in combination with topiramate, in linear and semi-logarithmic scale.
Figure 15:
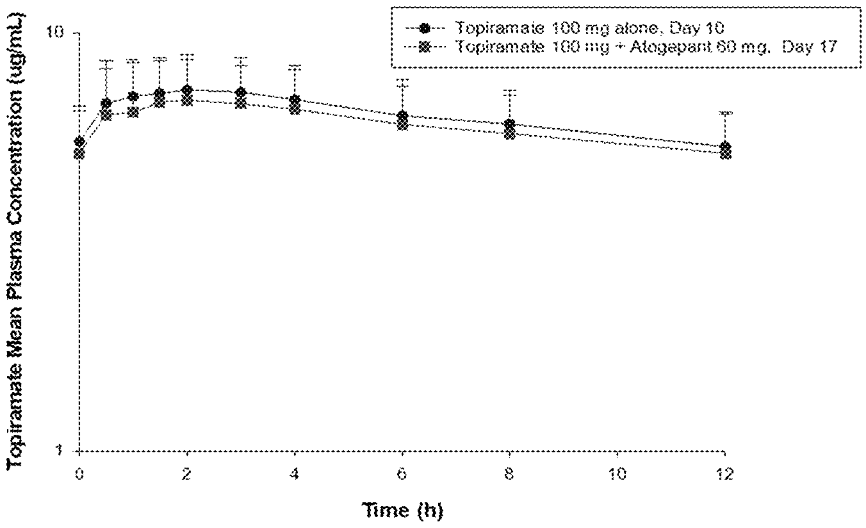

The mean (SD) steady state plasma concentrations of topiramate following administration alone and in combination with atogepant are shown in FIG. 15. Topiramate plasma concentrations were marginally lower when coadministered with atogepant compared with topiramate alone. Topiramate PK parameters are summarized in Table 19. Overall, topiramate PK parameters were generally similar with and without coadministration of atogepant; however, the median $T_{max,ss}$ of topiramate was delayed by 0.5 h when coadministered with atogepant. The analysis of GMRs showed that topiramate $AUC_{0\text{-}tau,ss}$ and $C_{max,ss}$ were reduced by 5% and 6%, respectively, with atogepant coadministration, as shown in Table 20. The GMRs and their 90% CIs for the $C_{max}$ and AUC values were contained within the range 0.80 and 1.25, indicating no DDI.

TABLE 19

| Mean (±SD) PK parameters of topiramate alone (day 10) and when coadministered with atogepant (day 17) | | |
|---|---|---|
| PK Parameter | Topiramate 100 mg BID n = 24 | Topiramate 100 mg BID + Atogepant 60 mg QD n = 22 |
| $T_{max, ss}$ (h) | 1.5 (0-4)[a] | 2.0 (0-4)[a] |
| $C_{max, ss}$ (μg/mL) | 7.7 (1.6) | 7.3 (1.8) |

TABLE 19-continued

| Mean (±SD) PK parameters of topiramate alone (day 10) and when coadministered with atogepant (day 17) | | |
|---|---|---|
| PK Parameter | Topiramate 100 mg BID n = 24 | Topiramate 100 mg BID + Atogepant 60 mg QD n = 22 |
| $AUC_{0\text{-}tau, ss}$ (h · μg/mL) | 76.5 (15.7) | 72.6 (16.9) |
| $C_{min, ss}$ (μg/mL) | 5.2 (1.2) | 4.7 (1.4) |
| $C_{avg, ss}$ (μg/mL) | 6.4 (1.3) | 6.0 (1.4) |

[a]Median (min-max)

AUC0-tau,ss, area under the plasma concentration vs time curve during dosing interval at steady state; BID, twice daily; Cavg,ss, average plasma drug concentration at steady state; Cmax,ss, maximum plasma drug concentration at steady state; Cmin,ss, minimum plasma drug concentration at steady state; PK, pharmacokinetic; QD, once daily; SD, standard deviation; Tmax,ss, time of maximum plasma concentration at steady state.

TABLE 20

| Statistical Analysis of PK Parameters: Comparison of Plasma Topiramate Alone and Coadministered with Atogepant | | | |
|---|---|---|---|
| Atogepant PK Parameter | Topiramate Alone Geometric LSM | Topiramate and Atogepant Geometric LSM | GMRs (90% CI) (Combination/Alone) |
| $AUC_{0\text{-}tau,\ ss}$ (h · μg/mL) | 74.4 | 70.3 | 0.95 (0.88, 1.01) |
| $C_{max,\ ss}$ (μg/mL) | 7.5 | 7.0 | 0.94 (0.87, 1.01) |

$AUC_{0\text{-}tau,ss}$, area under the plasma concentration vs time curve during dosing interval at steady state; CI, confidence interval; $C_{max,ss}$, maximum plasma drug concentration at steady state; GMR, geometric mean ratio; LSM, least-square mean; PK, pharmacokinetic.

Topiramate $AUC_{0\text{-}tau,ss}$ and $C_{max,ss}$ were similar upon coadministration with atogepant as compared to topiramate alone, whereas the $AUC_{0\text{-}tau,ss}$ and $C_{max,ss}$ of atogepant decreased by 25% and 24%, respectively, due to mild induction of CYP3A4 by topiramate. However, these changes are expected to have minimal clinical significance and suggest no dose adjustment is necessary with coadministration of atogepant and mild CYP3A4 inducers.

For cohort 1 participants, the mean (SD) duration of exposure was 7.9 (0.42) days with atogepant alone, 8.8 (2.79) days of atogepant and topiramate coadministration, and 15.1 (3.62) days overall. For cohort 2 participants, the mean (SD) duration of exposure was 10.0 (0.20) days with topiramate alone, 6.7 (1.23) days of topiramate and atogepant coadministration, and 16.4 (1.96) days overall. A total of 24 participants (85.7%) in cohort 1 and 19 participants (76.0%) in cohort 2 reported at least 1 treatment-emergent adverse event (TEAE). TEAEs in the safety population are summarized in Table 6.

TABLE 6

| Overall Summary of TEAEs (Safety Population) | | | | |
|---|---|---|---|---|
| | Cohort 1 | | Cohort 2 | |
| Event, n (%) | Atogepant Alone n = 28 | Atogepant + Topiramate n = 26 | Topiramate Alone n = 25 | Topiramate + Atogepant n = 24 |
| TEAEs | 20 (71.4) | 17 (65.4) | 16 (64.0) | 13 (54.2) |
| Treatment-related TEAEs | 11 (39.3) | 14 (53.8) | 13 (52.0) | 10 (41.7) |
| Deaths | 0 (0) | 0 (0) | 0 (0) | 0 (0) |
| TESAEs | 0 (0) | 0 (0) | 0 (0) | 0 (0) |
| Treatment-related TESAEs | 0 (0) | 0 (0) | 0 (0) | 0 (0) |
| TEAEs leading to discontinuation | 5 (17.9)[a] | 1 (3.8)[a] | 2 (8.0) | 1 (4-2) |

[a]One participant reported a TEAE during atogepant administration and a TEAE during combination of atogepant and topiramate.

The most commonly reported adverse events were nausea and constipation. Nausea was reported by 6 participants receiving atogepant alone and by 2 participants during atogepant and topiramate coadministration in cohort 1. In cohort 2, nausea was reported by 3 participants receiving topiramate alone and by 0 participants during topiramate and atogepant coadministration. Constipation was reported by 3 participants receiving atogepant alone and by 0 participants during atogepant and topiramate coadministration in cohort 1. In cohort 2, constipation was reported by 2 participants receiving topiramate alone and by 2 participants during topiramate and atogepant coadministration.

Five participants experienced a TEAE during administration of atogepant alone that led to discontinuation. One participant who reported increased aspartate aminotransferase/alanine aminotransferase and one participant who reported confusional state and insomnia discontinued during the atogepant alone study period. Two participants who experienced a TEAE during administration of atogepant alone (nausea and procedural pain [post lumbar puncture neck pain]; and post lumbar puncture syndrome) were able to complete atogepant dosing and discontinued the trial during the atogepant and topiramate coadministration period. One additional participant experienced a TEAE of nausea during administration of atogepant alone and a TEAE of muscular weakness during the atogepant and topiramate coadministration period; this participant discontinued during the coadministration period.

The incidence of treatment-related TEAEs was similar across treatment interventions and no serious AEs or deaths occurred during the trial. Clinical laboratory, vital sign, and ECG assessments revealed no clinically relevant findings and no participants met the criteria for a potential Hy's law case (aminotransferase >3 times the upper limit of normal [ULN], total bilirubin ≥2 times the ULN, and alkaline phosphatase <2 times ULN).

Administration of atogepant and topiramate, cither alone or in combination, is safe and well tolerated in healthy adults.

The invention claimed is:

1. A method for the preventive treatment of migraine in a patient undergoing concurrent treatment with an OATP inhibitor, the method comprising orally administering a therapeutically effective dose of 10 mg atogepant once daily to the patient, wherein the patient's migraines are safely and effectively treated.

2. The method according to claim 1, wherein co-administration of atogepant with the OATP inhibitor results in an increase in atogepant $C_{max}$ in the patient of about 2.2-fold relative to administration of atogepant alone.

3. The method according to claim 1, wherein co-administration of atogepant with the OATP inhibitor results in an increase in atogepant AUC in the patient of about 2.8-fold relative to administration of atogepant alone.

4. The method according to claim 1, wherein the OATP inhibitor is rifampin.

5. The method according to claim 1, wherein the migraine is episodic migraine.

6. A method for the preventive treatment of migraine in a patient undergoing concurrent treatment with an OATP inhibitor, the method comprising orally administering a therapeutically effective dose of 30 mg atogepant once daily to the patient, wherein the patient's migraines are safely and effectively treated.

7. The method according to claim 6, wherein co-administration of atogepant with the OATP inhibitor results in an increase in atogepant $C_{max}$ in the patient of about 2.2-fold relative to administration of atogepant alone.

8. The method according to claim 6, wherein co-administration of atogepant with the OATP inhibitor results in an increase in atogepant AUC in the patient of about 2.8-fold relative to administration of atogepant alone.

9. The method according to claim 6, wherein the OATP inhibitor is rifampin.

10. The method according to claim 6, wherein the migraine is episodic migraine.

* * * * *